United States Patent
Hirano et al.

[11] Patent Number: 6,087,390
[45] Date of Patent: Jul. 11, 2000

[54] DERIVATIVES OF ANTIFUNGAL SUBSTANCE BE-31405 AND PROCESS FOR PRODUCING THE SAME

[75] Inventors: Atsushi Hirano; Koichiro Torigoe; Hidenori Ogawa; Seigo Kamiya; Hiromasa Okada, all of Tsukuba; Masao Nagashima; Katsuhisa Kojiri, both of Tokyo; Hiroyuki Suda, Tsukuba, all of Japan

[73] Assignee: Banyu Pharmaceutical Co., Ltd., Tokyo, Japan

[21] Appl. No.: 09/423,643

[22] PCT Filed: May 20, 1998

[86] PCT No.: PCT/JP98/02218

§ 371 Date: Nov. 18, 1999

§ 102(e) Date: Nov. 18, 1999

[87] PCT Pub. No.: WO98/52957

PCT Pub. Date: Nov. 26, 1998

[30] Foreign Application Priority Data

May 20, 1997 [JP] Japan .................. 9-145919

[51] Int. Cl.$^7$ .................. A61K 31/35; C07D 311/02
[52] U.S. Cl. .................. 514/455; 514/454; 549/283
[58] Field of Search .................. 514/283; 549/454, 549/455

[56] References Cited

U.S. PATENT DOCUMENTS

| | | | |
|---|---|---|---|
| 4,636,520 | 1/1987 | Umio et al. | 514/399 |
| 5,120,735 | 6/1992 | Arika et al. | 514/252 |
| 5,922,709 | 7/1999 | Okada et al. | 514/241 |

FOREIGN PATENT DOCUMENTS

| | | |
|---|---|---|
| 0 712 859 | 5/1996 | European Pat. Off. |
| 61-56127 | 3/1986 | Japan . |
| 1-93525 | 4/1989 | Japan . |
| 6-15555 | 3/1994 | Japan . |
| 6-157582 | 6/1994 | Japan . |
| WO 97/18821 | 5/1997 | WIPO . |

OTHER PUBLICATIONS

Stephen J. Coval, et al., The Journal of Antibiotics, vol. 48, pp. 1171–1172, "SCH57404, an Antifungal Agent Possessing the Rare Sodaricin Skeleton and a Tricyclic Sugar Moiety", 1995.

G. Schneider, et al., National Product Letters, vol. 7, pp. 309–316, "Xylarin, an Antifungal Xylaria Metabolite with an Unusual Tricyclicuronic Acid Moiety", 1995.

*Primary Examiner*—Amelia Owens
*Attorney, Agent, or Firm*—Oblon, Spivak, McClelland, Maier & Neustadt, P.C.

[57] ABSTRACT

The present invention relates to a compound represented by general formula (I) or a pharmaceutically acceptable salt or ester thereof:

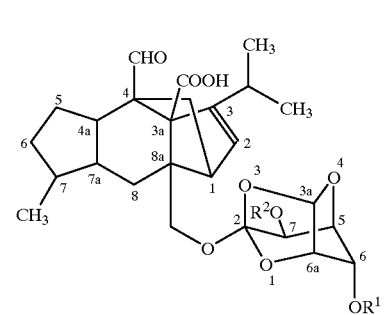

wherein each of $R^1$ and $R^2$ is independently a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has substituent(s), or a group represented by —Y—$R^3$ (provided that when $R^2$ is a hydrogen atom, $R^1$ is not a methyl group or an acetyl group; when $R^2$ is an acetyl group, $R^1$ is not a methyl group), an antifungal agent containing it as an active ingredient and an antifungal composition containing it and an azole type antifungal agent.

14 Claims, No Drawings

DERIVATIVES OF ANTIFUNGAL SUBSTANCE BE-31405 AND PROCESS FOR PRODUCING THE SAME

This application is a 371 of PCT/JP98/02218 filed on May 20, 1998.

TECHNICAL FIELD

The present invention is useful in the pharmaceutical field. More specifically, the present invention relates to a novel antifungal agent.

BACKGROUND ART

In the field of antifungal agents, a number of compounds have already come into practical use as pharmaceuticals. However, their effects on various harmful strains are not always satisfactory, and emergence of strains resistant to these pharmaceuticals, especially to azole type antifungal agents in wide use, has become a serious clinical problem. Therefore, development of pharmaceuticals effective against these harmful strains and resistant strains is demanded.

JP-A-6-157582, J. Antibiotics, vol. 48, pp.1171–1172 (1995) and Nat. Prod. Lett., vol. 7, pp.309–316 (1995) disclose structural analogues of the compounds of the present invention which show excellent antifungal action, but neither disclose nor suggest anything specific about the compounds of the present invention.

Further, the present inventors have recently found that compounds containing the compounds disclosed by the above-mentioned references and azole type antifungal agents have excellent antifungal action (PCT/JP96/00353).

However, development of even more excellent antifungal agents is still demanded.

DISCLOSURE OF THE INVENTION

The object of the present invention is to provide novel antifungal agents which meet the above-mentioned demand. Namely, the problem that the present invention is to solve is to provide agents which show antifungal action against various harmful strains and resistant strains against which conventional antifungal agents are not satisfactorily effective.

The present inventors have conducted extensive research to solve the above-mentioned problem, and as a result, have found that the compounds represented by general formula (I) and pharmaceutically acceptable salts or esters thereof have excellent antifungal activities, and the present invention has been accomplished.

Namely, the present invention provides a compound represented by general formula (I) or a pharmaceutically acceptable salt or ester thereof:

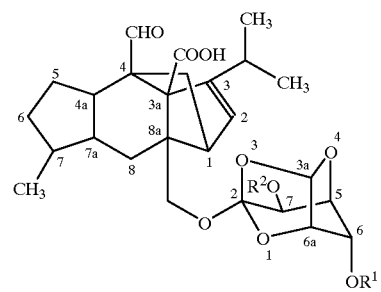

wherein each of $R^1$ and $R^2$ is independently a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —Y—$R^3$; Y is a carbonyl group, a thiocarbonyl group or a sulfonyl group; and $R^3$ is a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which is not substituted, or a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1$–$C_{16}$ alkyl group, a halo-$C_1$–$C_{16}$ alkyl group, a hydroxy-$C_1$–$C_{16}$ alkyl group, an amino-$C_1$–$C_{16}$ alkyl group, a carboxy-$C_1$–$C_{16}$ alkyl group or a protecting group (provided that when $R^2$ is a hydrogen atom, $R^1$ is not a methyl group or an acetyl group; when $R^2$ is an acetyl group, $R^1$ is not a methyl group) and an antifungal agent containing it as an active ingredient.

The present invention also provides an antifungal composition containing a compound represented by general formula (I) or a pharmaceutically acceptable salt or ester thereof and an azole type antifungal agent as active ingredients.

The symbols and terms used in the specification will be explained.

A $C_1$–$C_{16}$ alkyl group means a linear or branched alkyl group having a carbon number of 1 to 16, such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a decyl group, a dodecyl group or a hexadecyl group.

A $C_2$–$C_{10}$ alkenyl group means a linear or branched alkenyl group which has one to five double bonds and a carbon number of 2 to 10, such as a propenyl group, a 2-butenyl group, a 3-butenyl group, a 3-pentenyl group, a 4-hexenyl group or a 1,3-hexadienyl group.

A $C_3$–$C_6$ alkynyl group means a linear or branched alkynyl group which has one to three triple bonds and a carbon number of 3 to 6, such as a propynyl group, a 2-butynyl group, a 3-butynyl group, a 3-pentynyl group, a 4-hexynyl group or a 1-decynyl group.

A $C_6$–$C_{12}$ aryl group means a monocyclic or polycyclic aryl group having a carbon number of 6 to 12, such as a phenyl group, a naphthyl group or a tetrahydronaphthyl group.

A $C_6$–$C_{12}$ aryloxy group means an aryloxy group having the above-mentioned $C_6$–$C_{12}$ aryl group, such as a phenyloxy group, a naphthyloxy group or a tetrahydronaphthyloxy group.

A halogen atom means a fluorine atom, a chlorine atom, a bromine atom or an iodine atom.

A $C_1$–$C_{16}$ alkyloxy group means an alkyloxy group having the above-mentioned $C_1$–$C_{16}$ alkyl group, such as a methyloxy group, an ethyloxy group, a propyloxy group, an isopropyloxy group, a butyloxy group, an isobutyloxy group, a sec-butyloxy group, a tert-butyloxy group, a pentyloxy group, an isopentyloxy group, a neopentyloxy group, a hexyloxy group, a decyloxy group, a dodecyloxy group, a hexadecyloxy group or a cetyloxy group.

A $C_1$–$C_{16}$ alkyloxycarbonyl group means an alkyloxycarbonyl group having the above-mentioned $C_1$–$C_{16}$ alkyl group, such as a methyloxycarbonyl group, an ethyloxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isopentyloxycarbonyl group, a neopentyloxycarbonyl group, a hexyloxycarbonyl group, a decyloxycarbonyl group, a dodecyloxycarbonyl group or a hexadecyloxycarbonyl group.

A $C_1$–$C_{16}$ alkylcarbonyloxy group means an alkylcarbonyloxy group having the above-mentioned $C_1$–$C_{16}$ alkyl group, such as a methylcarbonyloxy group, an ethylcarbonyloxy group, a propylcarbonyloxy group, an isopropylcarbonyloxy group, a butylcarbonyloxy group, an isobutylcarbonyloxy group, a sec-butylcarbonyloxy group, a tert-butylcarbonyloxy group, a pentylcarbonyloxy group, an isopentylcarbonyloxy group, a neopentylcarbonyloxy group, a hexylcarbonyloxy group, a decylcarbonyloxy group, a dodecylcarbonyloxy group, a hexadecylcarbonyloxy group or a palmitoyloxy group.

A mono-$C_1$–$C_{16}$ alkylamino group means an amino group mono-substituted with the above-mentioned $C_1$–$C_{16}$ alkyl group, such as a methylamino group, an ethylamino group, a propylamino group, an isopropylamino group, a butylamino group, an isobutylamino group, a sec-butylamino group, a tert-butylamino group, a pentylamino group, an isopentylamino group, a neopentylamino group or a hexylamino group.

A di-$C_1$–$C_{16}$ alkylamino group means an amino group di-substituted with the above-mentioned $C_1$–$C_{16}$ alkyl groups, such as a dimethylamino group, an ethylmethylamino group, a diethylamino group, an ethylpropylamino group, a dipropylamino group, a butylmethylamino group, a dibutylamino group, butylethylamino group, a methylpentylamino group, a hexylmethylamino group or an ethylhexylamino group.

A $C_3$–$C_6$ cycloalkyl group means a cycloalkyl group having a carbon number of 3 to 6, such as a cyclopropyl group, a cyclobutyl group, a cyclopentyl group or a cyclohexyl group.

A $C_3$–$C_6$ cycloalkyl-$C_1$–$C_{16}$ alkyl group means the above-mentioned $C_1$–$C_{16}$ alkyl group substituted with the above-mentioned $C_3$–$C_6$ cycloalkyl group, such as a cyclopropylmethyl group, a cyclobutylmethyl group, a cyclopentylmethyl group, a cyclohexylmethyl group, a cyclopropylethyl group, a cyclobutylethyl group, a cyclopentylethyl group, a cyclohexylethyl group, a 3-cyclohexylpropyl group, a 3-cyclopentylpropyl group, a 4-cyclohexylbutyl group or a 4-cyclopentylbutyl group, and preferably has a total carbon number of 4 to 10.

A $C_7$–$C_{15}$ aralkyl group means the above-mentioned $C_1$–$C_{16}$ alkyl group substituted with the above-mentioned $C_6$–$C_{12}$ aryl group which has a carbon number of 7 to 15, such as a benzyl group, a phenethyl group, a phenylpropyl group, a phenybutyl group, a phenylpentyl group, a naphthylmethyl group or a naphthylethyl group.

A $C_7$–$C_{15}$ aralkyloxy group means an aralkyloxy group having the above-mentioned $C_7$–$C_{15}$ aralkyl group, such as a benzyloxy group, a phenethyloxy group, a phenylpropyloxy group, a phenylbutyloxy group, a phenylpentyloxy group, a naphthylmethyloxy group or a naphthylethyloxy group.

A heterocyclic group means an aromatic or non-aromatic 5 to 7-membered monocyclic heterocyclic group having one to four hetero atoms selected from the group consisting of nitrogen atoms, oxygen atoms and sulfur atoms or a condensed heterocyclic group having such a monocyclic heterocyclic group fused with the above-mentioned $C_3$–$C_6$ cycloalkyl group, the above-mentioned $C_6$–$C_{12}$ aryl group or another identical or different monocyclic heterocyclic group, such as a pyrrolyl group, a furyl group, a thienyl group, an oxazolyl group, an isoxazolyl group, a thiazolyl group, an isothiazolyl group, an imidazolyl group, a pyrazolyl group, an oxadiazoly group, a thiadiazoly group, a triazolyl group, a tetrazolyl group, a furazanyl group, a pyridyl group, a pyridazinyl group, a pyrimidinyl group, a pyrazinyl group, a triazinyl group, a dihydrothienyl group, a tetrahydrothienyl group, a pyrrolinyl group, a pyrrolidinyl group, an imidazolidinyl group, an imidazolinyl group, a piperidinyl group, a piperazinyl group, an oxazolinyl group, an isoxazolinyl group, an isoxazolidinyl group, a thiazolinyl group, a thiazolidinyl group, an isothiazolinyl group, an isothiazolidinyl group, a 1,2-dithiolanyl group, a 1,3-dithiolanyl group, a 1,2-dithiolyl group, a 1,3-dithiolyl group, a dihydrothiopyranyl group, a tetrahydrothiopyranyl group, a 1,4-dithianyl group, a 1,4-dithiinyl group, a 1,4-oxathiinyl group, a thiomorpholinyl group, a morpholinyl group, an indolyl group, an isoindolyl group, a quionolyl group, an isoquinolyl group, a quinolizinyl group, a cinnolinyl group, a quinoxalinyl group, a phthalazinyl group, a pteridinyl group, a purinyl group, a carbazolyl group, an acridinyl group, a phenazinyl group, a benzofuryl group, a chromanyl group, an isochromanyl group, a xanthenyl group, a benzoxazolyl group, an imidazothiazolyl group, a thieno[2,3-b]thienyl group or a 1,4-dithianaphthyl group.

A $C_7$–$C_{15}$ aralkylamino group means an aralkylamino group having the above-mentioned $C_7$–$C_{15}$ aralkyl group, such as a benzylamino group, a phenethylamino group, a phenylpropylamino group, a phenylbutylamino group, a phenylpentylamino group, a naphthylmethylamino group or a naphthylethylamino group.

A halo-$C_1$–$C_{16}$ alkyl group means the above-mentioned $C_1$–$C_{16}$ alkyl group substituted with one to three halogen atoms described above, such as a fluoromethyl group, a difluoromethyl group, a trifluoromethyl group, a 1-fluoroethyl group, a 2-fluoroethyl group, a 1,2-difluoroethyl group, a chloromethyl group, a dichloromethyl group, a 1-chloroethyl group, a 2-chloroethyl group, a 1,2-dichloroethyl group, a bromomethyl group, a dibromomethyl group, a 1-bromoethyl group, a 2-bromoethyl group or a 1,2-dibromoethyl group.

A hydroxy-$C_1$–$C_{16}$ alkyl group means the above-mentioned $C_1$–$C_{16}$ alkyl group substituted with one to three hydroxyl groups, such as a hydroxymethyl group, a 1-hydroxyethyl group, a 2-hydroxyethyl group, a 1,2-dihydroxyethyl group, a 1-hydroxypropyl group, a 2-hydroxypropyl group or a 3-hydroxypropyl group.

An amino-$C_1$–$C_{16}$ alkyl group means the above-mentioned $C_1$–$C_{16}$ alkyl group substituted with one to three amino groups, such as an aminomethyl group, a 1-aminoethyl group, a 2-aminoethyl group, a 1,2-diaminoethyl group, a 1-aminopropyl group, a 2-aminopropyl group or a 3-aminopropyl group.

A carboxy-$C_1$–$C_{16}$ alkyl group means the above-mentioned $C_1$–$C_{16}$ alkyl group substituted with one to three carboxyl groups, such as a carboxymethyl group, a 1-carboxyethyl group, a 2-carboxyethyl group, a 1,2-dicarboxyethyl group, a 1-carboxypropyl group, a 2-carboxypropyl group or a 3-carboxypropyl group.

A protecting group for a hydroxyl group is a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a p-nitrobenzyl group or a trityl group; or an acyl group such as a formyl group or an acetyl group, preferably a methoxymethyl group, a tetrahydropyranyl group, a trityl group, a tert-butyldimethylsilyl group or an acetyl group.

A protecting group for an amino group is aralkylidene group such as a benzylidene group, a p-chlorobenzylidene group or a p-nitrobenzylidene group; an aralkyl group such as a benzyl group, a p-methoxybenzyl group, a p-nitrobenzyl group, a benzhydryl group or a trityl group; a lower alkanoyl group such as formyl group, an acetyl group, a propionyl group, a butyryl group or a pivaloyl group; a lower haloalkanoyl group such as a trifluoroacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2,2,2-trichloroethoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a tert-butyldimethylsilyl group, preferably an acetyl group, a trifluoroacetyl group, a tert-butoxycarbonyl group or a benzyloxycarbonyl group.

A protecting group for a carboxyl group is a lower alkyl group such as a methyl group, an ethyl group, a propyl group, an isopropyl group or a tert-butyl group; a lower haloalkyl group such as a 2,2,2-trichloroethyl group; a lower alkenyl group such as a 2-propenyl group; or an aralkyl group such as a benzyl group, a p-methoxybenzyl group, a p-nitrobenzyl group, a benzhydryl group or a trityl group, preferably, a methyl group, an ethyl group, a tert-butyl group, a 2-propenyl group, a benzyl group, a p-methoxybenzyl group or a benzhydryl group.

A salt of the compound represented by general formula (I) may be a pharmaceutically acceptable common salt, which may be a base-addition salt resulting from addition of a base to an acidic group, if any, such as a carboxyl group at the 3a-position or any other acidic group, or an acid-addition salt resulting from addition of an acid to an amino group, if any, or a basic heterocyclic ring, if any.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonate such as a methanesulfonate, an isethionate, a benzenesulfonate or a p-toluenesulfonate.

An ester of the compound represented by general formula (I) may be a pharmaceutically acceptable common ester resulting from esterification of a carboxyl group at the 3a-position or any other carboxyl group, and may, for example, be an ester with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or a cyclopentyl group, an ester with aralkyl group such as a benzyl group or a phenethyl group, an ester with a lower alkenyl group such as an allyl group or a 2-butenyl group, an ester with a lower alkoxyalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxyalkyl group such as a carbamoyloxymethyl group, an ester with a phthalidyl group or an ester with a (5-substituted-2-oxo-1,3-dioxol-4-yl)methyl group such as a (5-methyl-2-oxo-1,3-dioxol-4-yl)methyl group.

An azole type antifungal agent is a compound which has an antifungal activity and an imidazole or triazole ring in its molecule, and is one or at least two selected from antifungal agents, for example, disclosed in Clinical Infectious Diseases, vol. 14 (Suppl 1), S161–9 (1992) such as butoconazole, oxiconazole, clotrimazole, terconazole, econazole, tioconazole, miconazole, fluconazole, ketoconazole and itraconazole, preferably miconazole, fluconazole or itraconazole. These agents are commercially available or obtainable in accordance with the above-mentioned reference.

The compounds represented by general formula (I) include the compounds represented by general formula (I-a):

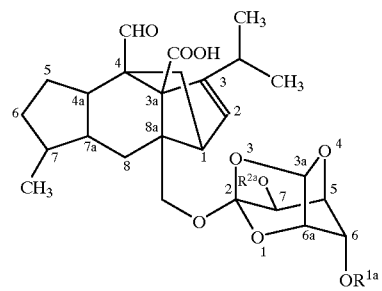

[I-a]

wherein $R^{1a}$ is a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a C$_7$–C$_{15}$ aralkyl group or a heterocyclic group which is not substituted, a C$_1$–C$_{16}$ alkyl group, a C$_2$–C$_{10}$ alkenyl group, a C$_3$–C$_6$ alkynyl group, a C$_6$–C$_{12}$ aryl group, a C$_7$–C$_{15}$ aralkyl group or a heterocyclic group which has one to five substituents selected from the group consisting of halogen atoms, cyano groups, hydroxyl groups, C$_1$–C$_{16}$ alkyloxy groups, C$_1$–C$_{16}$ alkylcarbonyloxy groups, amino groups, mono-C$_1$–C$_{16}$ alkylamino groups, di-C$_1$–C$_{16}$ alkylamino groups, carboxyl groups, C$_1$–C$_{16}$ alkyloxycarbonyl groups, aminocarbonyl groups, sulfo groups, C$_6$–C$_{12}$ aryl groups, C$_6$–C$_{12}$ aryloxy groups, C$_7$–C$_{15}$ aralkyloxy groups and heterocyclic groups, or a group represented by —Y$^a$—R$^{3a}$; Y$^a$ is a carbonyl group, a thiocarbonyl group or a sulfonyl group; R$^{3a}$ is a C$_1$–C$_{16}$ alkyl group, a C$_2$–C$_{10}$ alkenyl group, a C$_3$–C$_6$ cycloalkyl group, a C$_3$–C$_6$ cycloalkyl-C$_1$–C$_{16}$ alkyl group, a C$_6$–C$_{12}$ aryl group, a C$_7$–C$_{15}$ aralkyl group, a C$_7$–C$_{15}$ aralkylamino group or a heterocyclic group which is not substituted, or a C$_1$–C$_{16}$ alkyl group, a C$_2$–C$_{10}$ alkenyl group, a C$_3$–C$_6$ cycloalkyl group, a C$_3$–C$_6$ cycloalkyl-C$_1$–C$_{16}$ alkyl group, a C$_6$–C$_{12}$ aryl group, a C$_7$–C$_{15}$ aralkyl group, a C$_7$–C$_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a C$_1$–C$_{16}$ alkyl group, a halo-C$_1$–C$_{16}$ alkyl group, a hydroxy-C$_1$–C$_{16}$ alkyl group, an amino-C$_1$–C$_{16}$ alkyl group, a carboxy-C$_1$–C$_{16}$ alkyl group or a protecting group; R$_{2a}$ is a C$_1$–C$_{16}$ alkyl group, a C$_2$–C$_{10}$ alkenyl group, a C$_3$–C$_6$ alkynyl group, a C$_6$–C$_{12}$ aryl group, a C$_7$–C$_{15}$ aralkyl group or a heterocyclic group which is not substituted, a C$_1$–C$_{16}$ alkyl group, a C$_2$–C$_{10}$ alkenyl group, a C$_3$–C$_6$ alkynyl group, a C$_6$–C$_{12}$ aryl group, a C$_7$–C$_{15}$ aralkyl group or a heterocyclic group which has one to five substituents selected from the group consisting of halogen atoms, cyano groups, hydroxyl groups, C$_1$–C$_{16}$ alkyloxy groups, C$_1$–C$_{16}$ alkylcarbonyloxy groups, amino groups, mono-C$_1$–C$_{16}$ alkylamino groups, di-C$_1$–C$_{16}$ alkylamino groups, carboxyl groups, C$_1$–C$_{16}$ alkyloxycarbonyl groups, aminocarbonyl groups, sulfo groups, C$_6$–C$_{12}$ aryl groups, C$_6$–C$_{12}$ aryloxy groups, C$_7$–C$_{15}$ aralkyloxy groups and heterocyclic groups, or a group represented by —Y$^b$—R$^{3b}$; Y$^b$ is a carbonyl group, a thiocarbonyl group or a sulfonyl group; and R$^{3b}$ is a C$_1$–C$_{16}$ alkyl group, a C$_2$–C$_{10}$ alkenyl group, a C$_3$–C$_6$ cycloalkyl group, a C$_3$–C$_6$ cycloalkyl-C$_1$–C$_{16}$ alkyl group, a C$_6$–C$_{12}$ aryl group, a C$_7$–C$_{15}$ aralkyl group, a C$_7$–C$_{15}$ aralkylamino group or a heterocyclic group which is not substituted, or a C$_1$–C$_{16}$ alkyl group, a C$_2$–C$_{10}$ alkenyl group, a C$_3$–C$_6$ cycloalkyl group, a C$_3$–C$_6$ cycloalkyl-C$_1$–C$_{16}$ alkyl group, a C$_6$–C$_{12}$ aryl group, a C$_7$–C$_{15}$ aralkyl group, a C$_7$–C$_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a C$_1$–C$_{16}$ alkyl group, a halo-C$_1$–C$_{16}$ alkyl group, a hydroxy-C$_1$–C$_{16}$ alkyl group, an amino-C$_1$–C$_{16}$ alkyl group, a carboxy-C$_1$–C$_{16}$ alkyl group or a protecting group (provided that when Y$^b$ is a carbonyl group, and R$^{3b}$ is a C$_1$–C$_{16}$ alkyl group which is not substituted, R$^{1a}$ is not a C$_1$–C$_{16}$ alkyl group which is not substituted), the compounds represented by general formula (I-b):

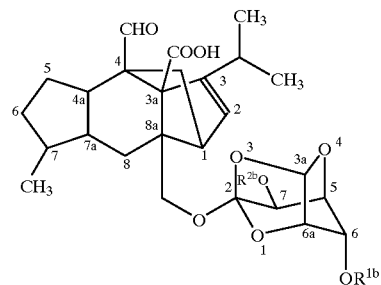

[I-b]

wherein R$^{1b}$ is a C$_1$–C$_{16}$ alkyl group which is not substituted; R$^{2b}$ is a group represented by —Y$^c$—R$^{3c}$; Y$^c$ is a carbonyl group; and R$^{3c}$ is a C$_1$–C$_{16}$ alkyl group which is not substituted (provided that both R$^{1b}$ and R$^{3c}$ are not methyl groups at the same time), the compounds represented by general formula (I-c):

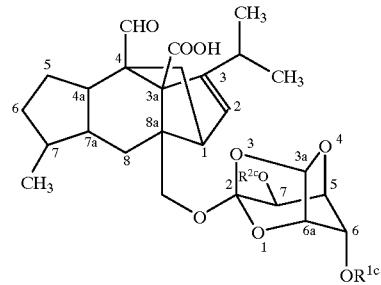

[I-c]

wherein R$^{1c}$ is a hydrogen atom, a C$_2$–C$_{10}$alkenyl group, a C$_3$–C$_6$ alkynyl group, a C$_6$–C$_{12}$ aryl group, a C$_7$–C$_{15}$ aralkyl group or a heterocyclic group, or a C$_1$–C$_{16}$ alkyl group, a C$_2$–C$_{10}$ alkenyl group, a C$_3$–C$_6$ alkynyl group, a C$_6$–C$_{12}$ aryl group, a C$_7$–C$_{15}$ aralkyl group or a heterocyclic group which has one to five substituents selected from the group consisting of halogen atoms, cyano groups, hydroxyl groups, C$_1$–C$_{16}$ alkyloxy groups, C$_1$–C$_{16}$ alkylcarbonyloxy groups, amino groups, mono-C$_1$–C$_{16}$ alkylamino groups, di-C$_1$–C$_{16}$ alkylamino groups, carboxyl groups, C$_1$–C$_{16}$ alkyloxycarbonyl groups, aminocarbonyl groups, sulfo groups, C$_6$–C$_{12}$ aryl groups, C$_6$–C$_{12}$ aryloxy groups, C$_7$–C$_{15}$ aralkyloxy groups and heterocyclic groups, or a group represented by —Y—R$^3$; Y is a carbonyl group, a thiocarbonyl group or a sulfonyl group; R$^3$ is a C$_1$–C$_{16}$ alkyl group, a C$_2$–C$_{10}$ alkenyl group, a C$_3$–C$_6$ cycloalkyl group, a C$_3$–C$_6$ cycloalkyl-C$_1$–C$_{16}$ alkyl group, a C$_6$–C$_{12}$ aryl group, a C$_7$–C$_{15}$ aralkyl group, a C$_7$–C$_{15}$ aralkylamino group or a heterocyclic group which is not substituted, or a C$_1$–C$_{16}$ alkyl group, a C$_2$–C$_{10}$ alkenyl group, a C$_3$–C$_6$ cycloalkyl group, a C$_3$–C$_6$ cycloalkyl-C$_1$–C$_{16}$ alkyl group, a C$_6$–C$_{12}$ aryl group, a C$_7$–C$_{15}$ aralkyl group, a C$_7$–C$_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a C$_1$–C$_{16}$ alkyl group, a halo-C$_1$–C$_{16}$ alkyl group, a hydroxy-C$_1$–C$_{16}$ alkyl group, an amino-C$_1$–C$_{16}$ alkyl group, a carboxy-C$_1$–C$_{16}$ alkyl group or a protecting group; and R$^{2c}$ is a hydrogen atom (provided that when Y is a carbonyl group, $R^3$ is not a $C_1$–$C_{16}$ alkyl group which is not substituted), the compounds represented by general formula (I-d):

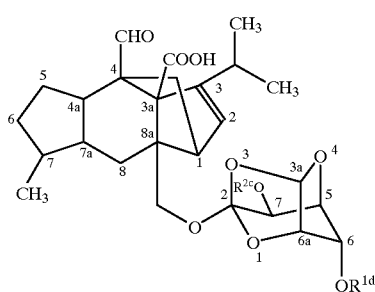

[I-d]

wherein $R^{1d}$ is a $C_1$–$C_{16}$ alkyl group which is not substituted; and $R^{2c}$ is a hydrogen atom (provided that $R^{1d}$ is not a methyl group) and the compounds represented by general formula (I-e):

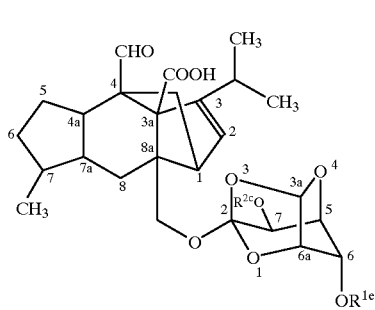

[I-e]

wherein $R^{1e}$ is a group represented by —$Y^c$—$R^{3d}$; $Y^c$ is a carbonyl group; $R^{3d}$ is a $C_1$–$C_{16}$ alkyl group which is not substituted; and $R^{2c}$ is a hydrogen atom (provided that $R^{3d}$ is not a methyl group).

Among the compounds represented by general formula (I), preferred are those wherein $R^1$ is a hydrogen atom, an unsubstituted $C_1$–$C_{16}$ alkyl group such as an ethyl group, a propyl group, an isopropyl group, a butyl group, a pentyl group, an isopentyl group, a hexyl group, a decyl group or a cetyl group, preferably a butyl group, a pentyl group, an isopentyl group, a hexyl group or a decyl group, an unsubstituted $C_2$–$C_{10}$ alkenyl group such as a 3-methyl-2-butenyl group, an unsubstituted $C_7$–$C_{15}$ aralkyl group such as a benzyl group; a $C_1$–$C_{16}$ alkyl group or a $C_3$–$C_6$ alkynyl group which has one to five substituents selected from the group consisting of cyano groups, $C_1$–$C_{16}$ alkyloxycarbonyl groups, aminocarbonyl groups, $C_6$–$C_{12}$ aryl groups, $C_6$–$C_{12}$ aryloxy groups, $C_7$–$C_{15}$ aralkyloxy groups and heterocyclic groups such as a 3-cyanopropyl group, an ethoxycarbonylmethyl group, an aminocarbonylmethyl group, a 3-phenoxypropyl group, a 3-benzyloxypropyl group, a 4-pyridylmethyl group, a 2-(N-piperidino)ethyl group, a 3-(N-1H-pyrrolo)propyl group or a phenylacetyl group; or a group represented by —Y—$R^3$ wherein Y is a carbonyl group, and $R^3$ is an unsubstituted $C_1$–$C_{16}$ alkyl group, an unsubstituted $C_2$–$C_{10}$ alkenyl group, an unsubstituted $C_6$–$C_{12}$ aryl group, an unsubstituted $C_7$–$C_{15}$ aralkyl group, an unsubstituted $C_7$–$C_{15}$ aralkylamino group or a $C_1$–$C_{16}$ alkyl group having one to four carboxyl groups such as a propionyl group, a butyryl group, a valeryl group, a 3-methylbutyryl group, a hexanoyl group, a heptanoyl group, a decanoyl group, a lauroyl group or a palmitoyl group, preferably, a butyryl group, a valeryl group, a hexanoyl group, a heptanoyl group or a decanoyl group, or a crotonoyl group, a 2,4-hexadienoyl group, a benzoyl group, a 3-phenylpropionyl group, a benzylaminocarbonyl group or a 3-carboxypropionyl group, $R^2$ is a hydrogen atom or a group represented by —Y—$R^3$ wherein Y is a carbonyl group, and $R^3$ is an unsubstituted $C_1$–$C_{16}$ alkyl group, an unsubstituted $C_6$–$C_{12}$ aryl group or a $C_1$–$C_{16}$ alkyl group having one to four carboxyl groups such as a propionyl group, a valeryl group, a heptanoyl group, a decanoyl group, a benzoyl group or a 3-carboxypropionyl group.

Among the compounds represented by general formula (I-d), preferred are those wherein $R^{1d}$ is an unsubstituted $C_4$–$C_{10}$ alkyl group, particularly a butyl group, a pentyl group, an isopentyl group, a hexyl group or a decyl group.

Among the compounds represented by general formula (I-e), preferred are those wherein $R^{3d}$ is an unsubstituted $C_3$–$C_9$ alkyl group, particularly a propyl group, a butyl group, a pentyl group, a hexyl group or a nonyl group.

The compounds of the present invention represented by general formula (I) can be prepared, for example, by the following process.

Namely, the compounds of the present invention can be prepared by chemical modification of BE-31405 as the starting material into a compound represented by general formula (I) wherein $R^1$ or $R^2$ is a hydrogen atom and then introducing a substituent corresponding to $R^1$ or $R^2$ in a compound of the present invention instead of the hydrogen atom.

In the preparation, it is preferred to protect a functional group which does not participate in the reaction, if necessary, and deprotect it after the reaction.

For introduction of these substituents, well-known chemical techniques such as alkylation, alkenylation, aralkylation, alkanoylation, arylation, thiocarbonylation and sulfonylation may be used.

These terms should be interpreted broadly and cover any reactions for introduction of substituents corresponding to $R^1$ and $R^2$ in a compound represented by general formula (I) of the present invention. For example, alkanoylation means introduction of a substituted or unsubstituted alkanoyl group defined in the present invention.

Alkylation, alkenylation, alkynylation or aralkylation of a compound wherein $R^1$ or $R^2$ is a hydrogen atom can be accomplished in accordance with known methods using, for example, an alkylation, alkenylation, alkynylation or aralkylation agent such as an alkyl halide, an alkenyl halide, an alkynyl halide, an aralkyl halide, an alkyl mesylate, an alkenyl mesylate, an aralkyl mesylate, an alkyl tosylate or an aralkyl tosylate.

Alkylation, alkenylation, alkynylation or aralkylation of a compound wherein $R^1$ or $R^2$ is a hydrogen atom can be accomplished by treating the compound wherein $R^1$ or $R^2$ is a hydrogen atom with an alkylation, alkenylation, alkynylation or aralkylation agent in an appropriate solvent.

The solvent may be dimethylformamide, methylene chloride, dimethyl sulfoxide or a mixture thereof.

The reaction temperature is usually within a range of from about –20° C. to the boiling point of the solvent, preferably from 20° C. to 60° C., though it may be below the range, if necessary.

The reaction time is usually from 10 minutes to 24 hours, preferably from 1 hour to 12 hours, though it may be longer or shorter, if necessary.

The amount of an alkylation, alkenylation, alkynylation or aralkylation agent used for a compound wherein $R^1$ or $R^2$ is a hydrogen atom is usually at least 1 mole, preferably from 1 to 10 moles, more preferably from 2 to 5 moles in relation to the compound wherein $R^1$ or $R^2$ is a hydrogen atom, though it may be varied widely according to the kind of the compound or the reaction conditions without any restriction.

Alkanoylation or alkylthiocarbonylation of a compound wherein $R^1$ or $R^2$ is a hydrogen atom can be accomplished by treating the compound wherein $R^1$ or $R^2$ is a hydrogen atom with an acid halide or an acid anhydride corresponding to a given substituent in an appropriate solvent.

The solvent may be dimethylformamide, pyridine, methylene chloride, dimethyl sulfoxide or a mixture thereof.

The reaction temperature is usually within a range of from about −5° C. to the boiling point of the solvent, preferably from 20° C. to 60° C., though it may be below the range, if necessary.

The reaction time is usually from 30 minutes to 2 days, preferably from 1 hour to 24 hours, though it may be longer or shorter, if necessary.

The amount of an acid halide or an acid anhydride used for a compound wherein $R^1$ or $R^2$ is a hydrogen atom is usually at least 1 mole, preferably from 1 to 5 moles, more preferably from 1 to 3 moles in relation to the compound wherein $R^1$ or $R^2$ is a hydrogen atom, though it may be varied widely according to the kind of the compound or the reaction conditions without any restriction.

Sulfonylation of a compound wherein $R^1$ or $R^2$ is a hydrogen atom can be accomplished by treating the compound wherein $R^1$ or $R^2$ is a hydrogen atom with an organic sulfonyl halide or an organic sulfonic anhydride corresponding to a given substituent in an appropriate solvent in the presence or absence of a base.

The solvent may be dimethylformamide, methylene chloride, dimethyl sulfoxide or a mixture thereof.

The base may be sodium hydride or lithium hydride.

The reaction temperature is usually within a range of from about −10° C. to about 50° C., preferably from 20° C. to 60° C., though it may be below the range, if necessary.

The reaction time is usually from 30 minutes to 3 days, preferably from 1 hour to 24 hours, though it may be longer or shorter, if necessary.

The amount of an organic sulfonyl halide or an organic sulfonic anhydride used for a compound wherein $R^1$ or $R^2$ is a hydrogen atom is usually a small excess, preferably from 1 to 3 moles in relation to the compound wherein $R^1$ or $R^2$ is a hydrogen atom, though it may be varied widely according to the kind of the compound or the reaction conditions without any restriction.

In the above-mentioned methods, the protecting groups for functional groups which do not participate in the reaction may be protecting groups for a hydroxyl group, protecting groups for an amino group and protecting groups for a carboxyl group as described above or the like.

Introduction and elimination of the protecting groups can be accomplished by the methods disclosed in the literature (Protective Groups in Organic Synthesis, written by T. W. Greene, published by John Wiley & Sons (1981)) or similar methods or any ordinary methods widely known in the field of chemistry.

The compounds produced by the above-mentioned reactions can be isolated or purified through techniques already known in the field of organic chemistry such as precipitation, extraction with solvent, recrystallization and chromatography.

The compounds produced by the above-mentioned reactions can be converted into pharmaceutically acceptable salts or esters thereof or vice versa by ordinary methods.

The starting material, BE-31405, can be obtained, for example, by using microorganisms such as Penicillium sp. F-31405, as disclosed in JP-A-6-157582, or its mutant strain more productive of the compound, Penicillium sp. F31405-17M.

Penicillium sp. F31405-17M has the following mycological characteristics.

(1) Morphology

The F31405-17M strain is the same in shape as its origin, Penicillium sp. F-31405, with conidiophores of 110 to 210×1.8 to 3.6 μm and a smooth surface or fine projections and forms symmetrical double verticillate penicilli. The metulae are 10.0 to 13.1×2.3 to 3.1 μm and grow in bunches of 4 to 8. The phialides are (9.7 to) 11.4 to 15.0×1.8 to 2.6 μm and verticillate. The conidia have smooth surfaces and are subspherical or elliptic or ovoid and 3.5 to 4.4×2.6 to 3.5 μm in size.

(2) Culture Characteristics

The culture characteristics of the F31405-17M strain are slightly different from those of its origin F-31405. Table 1 shows the growth characteristics observed after 7 days of incubation on various agar media at 25° C. The colors in the Table were identified on the basis of the names of colors in Methuen Handbook of Color, 3rd ed., (1984).

TABLE 1

Growth characteristics of the F31405-17M strain

| Culture medium | Diameter of colonies (mm) | Color of colonies | Color of the colony reverse | Colony texture |
| --- | --- | --- | --- | --- |
| Czapek agar | 13–15 | Pale green to grayish green | Pale green to grayish green | Slightly velutinous |
| Czapek-yeast extract agar | 17–20 | Yellowish white to dark green | Bright yellow to yellowish white | Slightly velutinous |
| Malt extract agar | 30–32 | Dark green | Yellowish gray to yellowish white | velutinous |

The strain develops enough conidia on any culture medium, especially on the malt extract agar and secretes nothing. The strain produces a bright yellow soluble pigment on the Czapek agar and the Czapek-yeast extract agar. The improved strain F31405-17M does not form premature sclerotium tissue when incubated at 37° C., like its origin Penicillium sp. F-31405 can.

The growth is poor at 37° C. than at 25° C. on any culture medium. The strain is viable in a temperature range of from 12 to 37° C. with the optimum growth temperature of 28.5° C., and in a pH range of from 2 to 11 with the optimum growth pH of about 6.5.

Penicillium sp. F-31405 and F31405-17M have been placed on international deposit in National Institute of Bioscience and Human-Technology (NIBH), Agency of Industrial Science and Technology, Ministry of International Trade and Industry (address: 1–3, Higashi 1-chome, Tsukuba-Shi, Ibaraki-ken 305, Japan) with the deposition numbers of FERM BP-5714 (date of original deposition: Oct. 20, 1992) and FERM BP-5716 (date of original deposition: Sep. 13, 1996), respectively.

Compounds of the present invention represented by general formula (I) have excellent antifungal actions, as is evident from the biological activities shown below. The actifungal effects against a fungus are shown in Table 2.

TABLE 2

Biological activities (antifungal activities) of BE-31405 derivatives

| Compound No.[a] | MIC (μg/ml)[b] |
|---|---|
| Compound 10 | 6.25 |
| Compound 13 | 3.13 |
| Compound 14 | 1.56 |
| Compound 38 | 3.13 |
| Compound 41 | 1.56 |
| Compound 44 | 3.13 |
| Compound 47 | 1.56 |
| Compound 50 | 3.13 |

[a]Under the same experimental conditions, the MIC of BE-31405 in single use was 50 μg/ml, and the MIC of SCH57404 (xylarin) in single use was 100 μg/ml.
[b]MICs were determined against *Candida albicans* IFO1385 after 2 days of incubation of the test strain at 37° C. on yeast-nitrogen base agar (containing 1% glucose and 0.25% dipotassium hydrogen phosphate, Difco).

Although as shown in Table 2, BE-31405 shows growth inhibitory activity against a certain kind of fungus in vitro especially under acidic conditions, the compound is severely restricted in practical medical use by its big drawback that the activity remarkably lowers under neutral conditions, considering that the pH of blood is around neutrality.

The compounds of the present invention are excellent compounds showing strong antifungal activities under neutral conditions imparted by chemical modification to BE-31405 as well as under acidic conditions and are quite useful as antifungal agents.

Combined use of an azole type antifungal agent with the compounds of the present invention additively and synergically intensifies the antifungal activities of the compounds of the present invention.

In the case of the above-mentioned combined use, a compound of the present invention and an azole type antifungal agent may be administered simultaneously or separately or after formulation of a composition containing them as a pharmaceutical.

The compound or antifungal composition of the present invention can be administered orally or parenterally in its clinical application, and it may be formulated to meet the administration mode by adding various pharmaceutically acceptable additives, as the case requires, and used as an antifungal agent.

The form for such formulation may, for example, be solid formulations such as tablets, capsules, granules, pills, troches, powders or suppositories, or liquid formulations such as syrups, elixirs, suspensions or injections, as well as aerosols, eyedrops, ointments, ophthalmic ointments, emulsions, creams, liniments or lotions. These formulations may be prepared in accordance with conventional methods commonly used in the field of drug formulations.

As the additives, various additives which are commonly used in the drug formulation field, can be used. For example, saccharides such as lactose or glucose, a starch from corn, wheat or rice, a vegetable oil such as soybean oil, peanuts oil or sesame oil, a fatty acid such as stearic acid, an inorganic salt such as magnesium metasilicate aluminate or anhydrous calcium phosphate, a synthetic polymer such as polyvinylpyrrolidone or polyalkylene glycol, a fatty acid salt such as calcium stearate or magnesium stearate, an alcohol such as stearyl alcohol or benzyl alcohol, a synthetic cellulose derivative such as methyl cellulose, carboxymethyl cellulose, ethyl cellulose or hydroxy-propylmethyl cellulose, or others such as water, gelatin, talc and gum arabic, may, for example, be mentioned.

Further, in the case of a liquid formulation, it may be in such a form that at the time of use, it is dissolved or suspended in water or in other suitable medium. Especially when administration is carried out by e.g. intramuscular injection, intravenous injection or subcutaneous injection, a suitable medium for such an injection may, for example, be distilled water for injection, a lidocaine hydrochloride aqueous solution (for intramuscular injection), physiological saline, an aqueous glucose solution, ethanol, liquid for intravenous injection (such as an aqueous solution of citric acid and sodium citrate) or an electrolyte solution (for intravenous drip and intravenous injection), or a mixed solution thereof. Further, a buffer or a preservative may be added.

These formulations may contain usually from 0.1 to 100 wt %, preferably from 5 to 100 wt %, of the active ingredient in the case of the above-mentioned solid formulations, and may contain from 0.1 to 10 wt %, preferably from 1 to 5 wt %, in the case of other formulations.

When the compounds of the present invention are used together with an azole type antifungal agent as a composition, the weight ratio of a compound represented by general formula (I) or a pharmaceutically acceptable salt or ester thereof to an azole type antifungal agent is from 0.001:1 to 1000:1, preferably 0.05:1 to 20:1.

A practically preferred dose of the compound or the antifungal composition of the present invention varies depending upon the type of the compound used, the type of the composition blended, the sex, age, weight, diseased degree and the particular section to be treated of the patient, but it is usually from 0.1 to 100 mg/kg in the case of oral administration and from 0.01 to 100 mg/kg in the case of parenteral administration, per adult per day. The number of times of administration varies depending upon the administration method and the symptom, but it is preferred to carry out the administration from one to five times per day.

As described above, the present invention provides a useful antifungal agent and, needless to say, a novel treatment for mycosis.

BEST MODE FOR CARRYING OUT THE INVENTION

Now, the present invention will be described in further detail with reference to Examples, Formulation Examples and Reference Examples, but the present invention is by no means restricted thereby.

In the following Examples, BE-31405 obtained in Reference Examples is referred to as compound (1), and a compound wherein $R^1$ and $R^2$ are hydrogen is referred to as compound (2).

EXAMPLE 1

Preparation of 8a-[[[6-(hydroxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (2)

1.02 g of compound (1) was dissolved in 60 ml of methanol, mixed with 28 ml of 0.1 N aqueous NaOH and allowed to react at room temperature for 50 minutes under stirring. The reaction solution was poured into 600 ml of 0.1 M sodium phosphate buffer (pH 5.57), and the product was extracted with 600 ml of ethyl acetate. The ethyl acetate layer was washed with 400 ml and 300 ml portions of water. The washed ethyl acetate layer was concentrated in vacuo to give 871.8 mg of compound (2) as a colorless powder.

Rf: 0.37 (Kieselgel 60F254, Merck, chloroform-methanol; 10:1).

FAB-MS(m/z): 513[M+Na]$^+$.

$^1$H-NMR($\delta$ ppm, 500 MHz, CDCl$_3$):9.68(1H, s), 6.13 (1H, brd, J=3.7 Hz), 5.73(1H, brd, J=3.0 Hz), 4.49(1H, m), 4.24(1H, m), 4.06(1H, t, J=3.7 Hz), 4.02(1H, d, J=9.8 Hz), 3.98(1H, d, J=9.8 Hz), 3.71(1H, brs), 2.82(1H, t, J=3.7 Hz), 2.34(1H, m), 1.95–2.12(5H, m), 1.86(1H, m), 1.76 (2H, m), 1.31(1H, d, J=12.8 Hz), 1.23(1H, m), 1.04(3H, d, J=6.7 Hz), 1.03(1H, m), 0.97(3H, d, J=6.7 Hz), 0.79 (3H, d, J=7.0 Hz).

EXAMPLE 2

Preparation of 8a-[[[6-(propionyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (7)

15 mg of compound (2) was dissolved in 1.0 ml of pyridine and stirred together with 7.9 μl of propionic anhydride at room temperature for 92 hours.

The reaction solution was concentrated in vacuo and charged onto a silica gel column (Kieselgel 60, Merck, 1.5φ×27 cm) and eluted with chloroform-methanol (50:1). The fraction containing the desired product was concentrated in vacuo to give 5.1 mg of compound (7) as a colorless oily substance.

Rf: 0.45 (Kieselgel 60F254, Merck, chloroform-methanol; 10:1).

FAB-MS(m/z): 547[M+H]$^+$.

$^1$H-NMR($\delta$ ppm, 500 MHz, CDCl$_3$):9.68(1H, s), 6.10 (1H, brd, J=3.7 Hz), 5.75(1H, brd, J=3.0 Hz), 4.75(1H, m), 4.71(1H, t, J=4.0 Hz), 4.39(1H, m), 4.01(1H, d, J=9.8 Hz), 3.96(1H, d, J=9.8 Hz), 3.69(1H, brs), 2.80(1H, t, J=3.7 Hz), 2.45(2H, m), 2.33(1H, m), 1.90–2.10(5H, m), 1.87(1H, m), 1.76(2H, m), 1.30(1H, d, J=12.5 Hz), 1.23(1H, m), 1.19(3H, t, J=7.6 Hz), 1.03(3H, d, J=6.7 Hz), 1.02(1H, m), 0.96(3H, d, J=6.7 Hz), 0.79(3H, d, J=6.7 Hz).

EXAMPLE 3

Preparation of 8a-[[[6,7-di(propionyloxy)tetrahydro-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (8)

In the silica gel chromatography in Example 2, the fraction containing the desired compound eluted earlier than compound (7) was concentrated to give 2.0 mg of compound (8).

Rf: 0.67 (Kieselgel 60F254, Merck, chloroform-methanol; 10:1).

FAB-MS(m/z): 603[M+H]$^+$.

$^1$H-NMR($\delta$ ppm, 500 MHz, CDCl$_3$):9.63(1H, s), 6.10 (1H, brd, J=3.7 Hz), 5.83(1H, brd, J=3.0 Hz), 5.02(1H, brs), 4.78(1H, m), 4.73(1H, t, J=4.0 Hz), 4.44(1H, m), 4.04(1H, d, J=9.8 Hz), 3.92(1H, d, J=9.8 Hz), 2.67(1H, t, J=3.7 Hz), 2.47(4H, m), 2.32(1H, m), 1.83–2.10(6H, m), 1.73(2H, m), 1.28(1H, d, J=12.8 Hz), 1.23(1H, m), 1.20(6H, t, J=7.6 Hz), 1.02(3H, d, J=6.7 Hz), 1.01(1H, m), 0.95(3H, d, J=6.7 Hz), 0.78(3H, d, J=6.7 Hz).

EXAMPLE 4

Preparation of 8a-[[[6-(n-butyryloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (9)

300 mg of compound (2) was dissolved in 1.5 ml of dry pyridine and stirred together with 130 μl of n-butyric anhydride at room temperature for 5 hours. The reaction solution was concentrated in vacuo, charged onto a silica gel column (Kieselgel 60, Merck, 1.5φ×30 cm) and eluted with 700 ml of n-hexane-ethyl acetate (1:1) and then with ethyl acetate. The fraction containing the desired product was concentrated in vacuo to give the crude desired compound. For further purification, it was subjected to silica gel column chromatography (Kieselgel 60, Merck, 1.5φ×30 cm) and eluted with chloroform-methanol (50:1). The fraction containing the desired product was concentrated to dryness to give 106 mg of compound (9).

Rf: 0.62 (Kieselgel 60F254, Merck, chloroform-methanol; 10:1).

FAB-MS(m/z): 561[M+H]$^+$.

$^1$H-NMR($\delta$ ppm, 500 MHz, CDCl$_3$):9.68(1H, s), 6.09 (1H, brd, J=3.7 Hz), 5.74(1H, brd, J=3.0 Hz), 4.76(1H, m), 4.70(1H, dd, J=4.6, 3.3 Hz), 4.39(1H, m), 3.99(1H, d, J=9.8 Hz), 3.97(1H, d, J=9.8 Hz), 3.68(1H, d, J=1.5 Hz), 2.79(1H, t, J=3.7 Hz), 2.40(2H, m), 2.32(1H, m), 1.90–2.10(5H, m), 1.87(1H, m), 1.75(2H, m), 1.70(2H, m), 1.29(1H, d, J=12.5 Hz), 1.23(1H, m), 1.02(3H, d, J=6.7 Hz), 1.02(1H, m), 0.99(3H, t, J=7.3 Hz), 0.95(3H, d, J=6.7 Hz), 0.78(3H, d, J=6.7 Hz).

EXAMPLE 5

Preparation of 8a-[[[6-(n-valeryloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (10)

20 mg of compound (2) was dissolved in 1.0 ml of pyridine and stirred together with 30.4 μl of n-valeric anhydride at room temperature. After 55 hours, 16.1 μl of n-valeric anhydride was added, and the reaction was conducted for another 17 hours. The reaction solution was concentrated in vacuo, charged onto a silica gel column (Kieselgel 60, Merck, 1.5φ×30 cm) and eluted with chloroform-methanol (100:1). The fraction containing the desired product was concentrated in vacuo to give the desired compound as a crude product.

For further purification, it was subjected to Sephadex LH-20 column chromatography (Pharmacia, 1.5φ×30 cm) and eluted with methanol. The fraction containing the desired product was concentrated to dryness to give 10.3 mg of compound (10).

Rf: 0.39 (Kieselgel 60F254, Merck, chloroform-methanol; 20:1).

FAB-MS(m/z): 575[M+H]$^+$.

$^1$H-NMR($\delta$ ppm, 500 MHz, CDCl$_3$):9.69(1H, s), 6.09 (1H, brd, J=3.7 Hz), 5.74(1H, brd, J=4.0 Hz), 4.76(1H, m), 4.69(1H, t, J=3.7 Hz), 4.39(1H, m), 4.00(1H, d, J=9.8 Hz), 3.97(1H, d, J=9.8 Hz), 3.68(1H, brs), 2.80(1H, t, J=3.7 Hz), 2.42(2H, m), 2.33(1H, m), 1.92–2.12(5H, m), 1.85(1H, m), 1.76(2H, m), 1.64(2H, m), 1.38(2H, m), 1.30(1H, d, J=12.5 Hz), 1.24(1H, m), 1.02(3H, d, J=6.7 Hz), 1.01(1H, m), 0.96(3H, d, J=6.7 Hz), 0.94(3H, t, J=7.3 Hz), 0.79(3H, d, J=6.7 Hz).

EXAMPLE 6

Preparation of 8a-[[[6,7-di(n-valeryloxy)tetrahydro-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (11)

In the silica gel chromatography in Example 5, the fraction containing the desired compound eluted earlier than compound (10) was concentrated to give 8.0 mg of compound (11).

Rf: 0.52 (Kieselgel 60F254, Merck, chloroform-methanol; 20:1).

FAB-MS(m/z): 659[M+H]$^+$.

$^1$H-NMR($\delta$ ppm, 500 MHz, CDCl$_3$):9.67(1H, s), 6.10 (1H, brd, J=3.7 Hz), 5.83(1H, brd, J=3.0 Hz), 5.01(1H, brs), 4.78(1H, m), 4.71(1H, t, J=4.0 Hz), 4.42(1H, m), 3.98(1H, d, J=9.8 Hz), 3.94(1H, d, J=9.8 Hz), 2.67(1H, t, J=3.7 Hz), 2.45(4H, m), 2.32(1H, m), 1.82–2.10(6H, m), 1.60–1.78(6H, m), 1.40(4H, m), 1.28(1H, d, J=12.8 Hz), 1.22(1H, m), 1.02(3H, d, J=6.7 Hz), 1.01(1H, m), 0.96(6H, d, J=7.6 Hz), 0.95(3H, d, J=6.7 Hz), 0.78 (3H, d, J=6.7 Hz).

EXAMPLE 7

Preparation of 8a-[[[6-(3-methylbutyryloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (12)

41.4 mg of compound (2) was dissolved in 0.3 ml of dry pyridine and stirred together with 14.2 μl of isovaleric anhydride at room temperature. After 43 hours, 7.1 μl of isovaleric anhydride was added, and the reaction was conducted for another 26 hours. The reaction solution was concentrated in vacuo, mixed with 2 ml of methanol and 0.2 ml of water and washed with 2 ml of n-hexane twice and with petroleum ether twice. The methanol layer was concentrated in vacuo, and the reaction product was dissolved in 1 ml of chloroform, charged onto a silica gel column (Kieselgel 60, Merck, 1.5φ×25 cm) and eluted with 150 ml of chloroform and then with chloroform-methanol (50:1). The fraction containing the desired product was concentrated in vacuo to give 10.6 mg of compound (12) as a colorless oily substance.

Rf: 0.42 (Kieselgel 60F254, Merck, chloroform-methanol; 10:1).

FAB-MS(m/z): 575[M+H]$^+$.

$^1$H-NMR(δ ppm, 500 MHz, CDCl$_3$):9.69(1H, s), 6.08 (1H, brd, J=3.7 Hz), 5.74(1H, brd, J=4.0 Hz), 4.78(1H, m), 4.68(1H, t, J=3.7 Hz), 4.39(1H, m), 3.99(1H, d, J=9.8 Hz), 3.95(1H, d, J=9.8 Hz), 3.68(1H, d, J=1.5 Hz), 2.80(1H, t, J=3.7 Hz), 2.31(3H, m), 1.83–2.16(6H, m), 1.75(2H, m), 1.30(1H, d, J=12.5 Hz), 1.23(1H, m), 1.02(3H, d, J=6.7 Hz), 1.02(1H, m), 1.00(6H, d, J=6.7 Hz), 0.94(3H, d, J=6.7 Hz), 0.78(3H, d, J=6.7 Hz).

EXAMPLE 8

Preparation of 8a-[[[6-(n-hexanoyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (13)

39.0 mg of compound (2) was dissolved in 0.3 ml of dry pyridine and stirred together with 15.6 μl of n-hexanoic anhydride at room temperature. After 43 hours, 7.8 μl of n-hexanoic anhydride was added, and the reaction was conducted for another 26 hours. The reaction solution was concentrated in vacuo, mixed with 1 ml of methanol and 0.1 ml of water and washed with 1.5 ml of n-hexane twice and with petroleum ether twice. The methanol layer was concentrated in vacuo, charged onto a silica gel column (Kieselgel 60, Merck, 1.5φ×25 cm) and eluted with 150 ml of chloroform and then with chloroform-methanol (50:1). The fraction containing the desired product was concentrated in vacuo to give 15.1 mg of compound (13) as a colorless oily substance.

Rf: 0.46 (Kieselgel 60F254, Merck, chloroform-methanol; 10:1).

FAB-MS(m/z): 589[M+H]$^+$.

$^1$H-NMR(δ ppm, 500 MHz, CDCl$_3$):9.69(1H, s), 6.09 (1H, brd, J=3.7 Hz), 5.75(1H, brd, J=4.0 Hz), 4.75(1H, m), 4.70(1H, t, J=3.7 Hz), 4.39(1H, m), 3.99(1H, d, J=9.8 Hz), 3.96(1H, d, J=9.8 Hz), 3.68(1H, d, J=1.5 Hz), 2.81(1H, t, J=3.7 Hz), 2.41(2H, m), 2.32(1H, m), 1.84–2.12(6H, m), 1.75(2H, m), 1.66(2H, m), 1.33(4H, m), 1.30(1H, d, J=12.5 Hz), 1.23(1H, m), 1.02(3H, d, J=6.7 Hz), 1.00(1H, m), 0.94(3H, d, J=6.7 Hz), 0.91(3H, t, J=7.3 Hz), 0.78(3H, d, J=6.7 Hz).

EXAMPLE 9

Preparation of 8a-[[[6-(n-heptanoyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (14)

30 mg of compound (2) was dissolved in 1.0 ml of pyridine and stirred together with 54.7 μl of n-heptanoic anhydride at room temperature. After 42 hours, 29.6 μl of n-heptanoic anhydride was added, and the reaction was conducted for another 7 hours. The reaction solution was concentrated in vacuo, charged onto a silica gel column (Kieselgel 60, Merck, 1.5φ×30 cm) and eluted with chloroform-methanol (100:1). The fraction containing the desired product was concentrated in vacuo to give the desired compound as a crude product. For further purification, it was subjected to Sephadex LH-20 column chromatography (Pharmacia, 1.5φ×90 cm) and eluted with methanol. The fraction containing the desired product was concentrated in vacuo to dryness to give 12.1 mg of compound (14).

Rf: 0.66 (Kieselgel 60F254, Merck, chloroform-methanol; 10:1).

FAB-MS(m/z): 603[M+H]$^+$.

$^1$H-NMR(δ ppm, 500 MHz, CDCl$_3$),:9.70(1H, s), 6.09 (1H, brd, J=3.7 Hz), 5.74(1H, brd, J=4.0 Hz), 4.75(1H, m), 4.70(1H, t, J=3.7 Hz), 4.39(1H, m), 3.99(1H, d, J=9.8 Hz), 3.96(1H, d, J=9.8 Hz), 3.68(1H, d, J=1.5 Hz), 2.80(1H, t, J=3.7 Hz), 2.41(2H, m), 2.32(1H, m), 1.82–2.10(6H, m), 1.74(2H, m), 1.64(2H, m), 1.20–1.40 (8H, m), 1.02(3H, d, J=6.7 Hz), 1.00(1H, m), 0.95(3H, d, J=6.7 Hz), 0.90(3H, t, J=7.3 Hz), 0.79(3H, d, J=6.7 Hz).

EXAMPLE 10

Preparation of 8a-[[[6,7-di(n-heptanoyloxy)tetrahydro-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (15)

In the silica gel chromatography in Example 9, the fraction containing the desired compound eluted earlier than compound (14) was concentrated to give the desired compound as a crude product.

For further purification, it was subjected to Sephadex LH-20 column chromatography (Pharmacia, 1.5φ×30 cm) and eluted with methanol. The fraction containing the desired product was concentrated in vacuo to dryness to give 8.3 mg of compound (15).

Rf: 0.80 (Kieselgel 60F254, Merck, chloroform-methanol; 10:1).

FAB-MS(m/z): 715[M+H]$^+$.

$^1$H-NMR(δ ppm, 500 MHz, CDCl$_3$),:9.63(1H, s), 6.08 (1H, brd, J=3.7 Hz), 5.82(1H, brd, J=3.0 Hz), 5.00(1H, brs), 4.78(1H, m), 4.71(1H, t, J=4.0 Hz), 4.41(1H, m), 3.98(1H, d, J=9.8 Hz), 3.92(1H, d, J=9.8 Hz), 2.67(1H, t, J=3.7 Hz), 2.43(4H, m), 2.32(1H, m), 1.82–2.10(6H, m), 1.58–1.78(6H, m), 1.20–1.40(14H, m), 1.02(3H, d, J=6.7 Hz), 1.00(1H, m), 0.92(3H, d, J=6.7 Hz), 0.88(6H, t, J=7.3 Hz), 0.78(3H, d, J=6.7 Hz).

EXAMPLE 11

Preparation of 8a-[[[6-(decanoyloxy)tetrahydro-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (16)

40 mg of compound (2) was dissolved in 0.5 ml of dry pyridine and stirred together with 40 mg of decanoic anhydride at room temperature for 72 hours. The reaction solution was concentrated in vacuo, charged onto a silica gel column (Kieselgel 60, Merck, 1.5φ×30 cm) and eluted with 500 ml of n-hexane-ethyl acetate (2:1) and 300 ml of chloroform-methanol (50:1) successively. The fraction containing the desired product was concentrated in vacuo to give the desired compound as a crude product.

For further purification, it was subjected to silica gel column chromatography (Kieselgel 60, Merck, 1.5φ×30 cm) and eluted with chloroform-methanol (50:1). The fraction containing the desired product was concentrated in vacuo to dryness to give 7.9 mg of compound (16).

Rf: 0.42 (Kieselgel 60F254, Merck, chloroform-methanol; 20:1).

FAB-MS(m/z): 645[M+H]$^+$.

$^1$H-NMR(δ ppm, 500 MHz, CDCl$_3$):9.68(1H, s), 6.10 (1H, brd, J=3.7 Hz), 5.74(1H, brd, J=4.0 Hz), 4.75(1H, m), 4.70(1H, t, J=3.7 Hz), 4.39(1H, m), 4.03(1H, d, J=9.8 Hz), 3.96(1H, d, J=9.8 Hz), 3.68(1H, brs), 2.80(1H, t, J=3.7 Hz), 2.41(2H, m), 2.33(1H, m), 1.94–2.12(5H, m), 1.86(1H, m), 1.77(2H, m), 1.66(2H, m), 1.20–1.40(14H, m), 1.03(3H, d, J=6.7 Hz), 1.03(1H, m), 0.96(3H, d, J=6.7 Hz), 0.88(3H, t, J=7.3 Hz), 0.79(3H, d, J=6.7 Hz).

EXAMPLE 12

Preparation of 8a-[[[6,7-di(decanoyloxy)tetrahydro-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (17)

In the first silica gel chromatography in Example 11, the fraction containing the desired compound eluted earlier than compound (16) was concentrated to give 5.1 mg of compound (17).

Rf: 0.57 (Kieselgel 60F254, Merck, chloroform-methanol; 20:1).

FAB-MS(m/z): 799[M+H]$^+$.

$^1$H-NMR(δ ppm, 500 MHz, CDCl$_3$):9.63(1H, s), 6.10 (1H, brd, J=3.7 Hz), 5.82(1H, brd, J=3.0 Hz), 5.00(1H, brs), 4.78(1H, m), 4.71(1H, t, J=4.0 Hz), 4.42(1H, m), 4.02(1H, d, J=9.8 Hz), 3.92(1H, d, J=9.8Hz), 2.67(1H, t, J=3.7 Hz), 2.43(4H, m), 2.32(1H, m), 1.82–2.10(6H, m), 1.60–1.80(6H, m), 1.20–1.40(26H, m), 1.02(3H, d, J=6.7 Hz), 1.00(1H, m), 0.94(3H, d, J=6.7 Hz), 0.88(6H, t, J=7.3 Hz), 0.78(3H, d, J=6.7 Hz).

EXAMPLE 13

Preparation of 8a-[[[6-(lauroyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (18)

49.8 mg of compound (2) was dissolved in 0.5 ml of dry pyridine and stirred together with 58.3 mg of lauric anhydride at room temperature for 24 hours. The reaction solution was concentrated in vacuo, charged onto a silica gel column (Kieselgel 60, Merck, 1.5φ×30 cm) and eluted with 800 ml of n-hexane-ethyl acetate-chloroform (2:1:1), 300 ml of n-hexane-ethyl acetate-chloroform (1:1:1) and 300 ml of chloroform-methanol (20:1) successively. The fraction containing the desired product was concentrated in vacuo to give the desired compound as a crude product.

For further purification, it was subjected to chromatography using a silica gel column (Kieselgel 60, Merck, 1.5φ×30 cm) and eluted with chloroform-methanol (50:1). The fraction containing the desired product was concentrated in vacuo to dryness to give 24 mg of compound (18).

Rf: 0.43 (Kieselgel 60F254, Merck, chloroform-methanol; 20:1).

FAB-MS(m/z): 673[M+H]$^+$.

$^1$H-NMR(δ ppm, 500 MHz, CDCl$_3$):9.68(1H, s), 6.10 (1H, brd, J=3.7 Hz), 5.74(1H, brd, J=4.0 Hz), 4.75(1H, m), 4.70(1H, t, J=4.0 Hz), 4.39(1H, m), 4. 02(1H, d, J=9.8 Hz), 3.96(1H, d, J=9.8 Hz), 3.68(1H, d, J=1.5 Hz), 2.80(1H, t, J=3.7 Hz), 2.41(2H, m), 2.33(1H, m), 1.94–2.12(5H, m), 1.86(1H, m), 1.76(2H, m), 1.65(2H, m), 1.20–1.40(18H, m), 1.03(3H, d, J=6.7 Hz), 1.02(1H, m), 0.96(3H, d, J=6.7 Hz), 0.88(3H, t, J=7.3 Hz), 0.79(3H, d, J=6.7 Hz).

EXAMPLE 14

Preparation of 8a-[[[6-(palmitoyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (19)

44.3 mg of compound (2) was dissolved in a mixture of 0.5 ml of dry pyridine and 0.2 ml of dry dichloromethane and stirred together with 37.8 mg of palmitic anhydride at room temperature. After 120 hours, 37.8 mg of palmitic anhydride in 0.3 ml of dichloromethane was added, and the reaction was conducted for another 24 hours.

The reaction solution was concentrated in vacuo, charged onto a silica gel column (Kieselgel 60, Merck, 1.5φ×25 cm) and eluted with 440 ml of n-hexane-ethyl acetate (2:1). The fraction containing the desired product was concentrated in vacuo to give 19.3 mg of the crude desired product. The crude desired product was further subjected to reversed phase chromatography (Capcell Pak C18 UG-120, Shiseido, 2.0φ×25 cm, 0.03% trifluoroacetic acid-acetonitrile [1:9], 3.0 ml/min), and the fraction containing the desired product was concentrated in vacuo to give 6.2 mg of compound (19) as a colorless oily substance.

Rf: 0.46 (Kieselgel 60F254, Merck, chloroform-methanol; 10:1).

FAB-MS(m/z): 729[M+H]$^+$.

$^1$H-NMR(δ ppm, 500 MHz, CDCl$_3$):9.69(1H, s), 6.10 (1H, brd, J=3.7 Hz), 5.74(1H, brd, J=4.0 Hz), 4.75(1H, m), 4.70(1H, t, J=4.0 Hz), 4.39(1H, m), 4.01(1H, d, J=9.8 Hz), 3.96(1H, d, J=9.8 Hz), 3.68(1H, d, J=1.5 Hz), 2.80(1H, t, J=3.7 Hz), 2.41(2H, m), 2.33(1H, m), 1.92–2.12(5H, m), 1.87(1H, m), 1.76(2H, m), 1.65(2H, m), 1.20–1.38(26H, m), 1.03(3H, d, J=6.7 Hz), 1.02(1H, m), 0.95(3H, d, J=6.7 Hz), 0.88(3H, t, J=7.3 Hz), 0.79(3H, d, J=6.7 Hz).

EXAMPLE 15

Preparation of 8a-[[[6-(3-carboxypropionyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (20)

20 mg of compound (2) was dissolved in 1.0 ml of pyridine and stirred together with 16.4 mg of succinic anhydride at room temperature. After 52 hours, 8.2 mg of succinic anhydride was added, and the reaction was conducted for another 20 hours. The reaction solution was concentrated in vacuo and subjected to reversed phase chromatography (Capcell Pak C18 UG-120, Shiseido, 2.0φ×25 cm, 0.05% trifluoroacetic acid-acetonitrile [6:4], flow rate 10.0 ml/min, detection 210 nm) for purification, and the desired fraction was recovered. The recovered fraction was poured into 100 ml of 0.1 M sodium phosphate buffer pH 5.5 and extracted with 100 ml of ethyl acetate. The ethyl acetate extract was concentrated in vacuo to give 4.0 mg of compound (20).

Rf: 0.26 (Kieselgel 60F254, Merck, chloroform-methanol; 10:1).

FAB-MS(m/z): 591[M+H]$^+$.

$^1$H-NMR(δ ppm, 500 MHz, CDCl$_3$):9.69(1H, s), 6.13 (1H, brd, J=3.7 Hz), 5.75(1H, brd, J=4.0 Hz), 4.74(2H, m), 4.41(1H, m), 3.99(1H, d, J=9.8 Hz), 3.96(1H, d, J=9.8 Hz), 3.70(1H, d, J=1.5 Hz), 2.81(1H, t, J=3.7 Hz), 2.74(4H, m), 2.32(1H, m), 1.94–2.12(5H, m), 1.85(1H, m), 1.76(2H, m), 1.31(1H, d, J=12.5 Hz), 1.24(1H, m), 1.03(3H, d, J=6.7 Hz), 1.02(1H, m), 0.96(3H, d, J=6.7 Hz), 0.79(3H, d, J=6.7 Hz).

EXAMPLE 16
Preparation of 8a-[[[6,7-di(3-carboxypropionyloxy) tetrahydro-2,5-methanofuro[2,3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid (21)

In the reversed phase chromatography in Example 15, the fraction containing the desired compound eluted later than compound (20) was poured into 100 ml of 0.1 M sodium phosphate buffer pH 5.5 and extracted with 100 ml of ethyl acetate. The ethyl acetate extract was concentrated in vacuo to give 12 mg of compound (21).

Rf: 0.18 (Kieselgel 60F254, Merck, chloroform-methanol; 10:1).

FAB-MS(m/z): 691[M+H]$^+$.

$^1$H-NMR(δ ppm, 500 MHz, CDCl$_3$):9.67(1H, s), 6.10 (1H, brd, J=3.7 Hz), 5.82(1H, brd, J=3.0 Hz), 4.98(1H, brs), 4.78(1H, t, J=4.0 Hz), 4.75(1H, m), 4.46(1H, m), 4.02(1H, d, J=9.8 Hz), 3.92(1H, d, J=9.8 Hz), 2.64–2.80(9H, m), 2.32(1H, m), 1.70–2.10(8H, m), 1.20–1.40(2H, m), 1.03(3H, d, J=6.7 Hz), 1.00(1H, m), 0.98 (3H, d, J=6.7 Hz), 0.78(3H, d, J=6.7 Hz).

EXAMPLE 17
Preparation of 8a-[[[6-(crotonoyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (22)

25 mg of compound (2) was dissolved in 1.0 ml of pyridine and stirred together with 31.5 mg of crotonic anhydride at room temperature for 18 hours. The reaction solution was concentrated in vacuo and subjected to reversed phase chromatography (Capcell Pak C18 UG-120, Shiseido, 2.0φ×25 cm, 0.05% trifluoroacetic acid-acetonitrile [5:5], flow rate 10.0 ml/min, detection 210 nm) for purification, and the desired fraction was recovered. The recovered fraction was poured into 100 ml of 0.1 M sodium phosphate buffer pH 5.5 and extracted with 100 ml of ethyl acetate. The ethyl acetate extract was concentrated in vacuo to give 4.0 mg of compound (22).

Rf: 0.46 (Kieselgel 60F254, Merck, chloroform-methanol; 20:1).

FAB-MS(m/z): 559[M+H]$^+$.

$^1$H-NMR(δ ppm, 500 MHz, CDCl$_3$):9.69(1H, s), 7.08 (1H, dq, J=15.5, 7.0 Hz), 6.11(1H, brd, J=3.7 Hz), 5.94 (1H, brd, J=15.5 Hz), 5.76(1H, brd, J=4.0 Hz), 4.77(2H, m), 4.42(1H, m), 4.02(1H, d, J=9.8 Hz), 3.95(1H, d, J=9.8 Hz), 3.70(1H, d, J=1.5 Hz), 2.81(1H, t, J=3.7 Hz), 2.32(1H, m), 1.90–2.12(5H, m), 1.93(3H, brd, J=7.0 Hz), 1.87(1H, m), 1.75(2H, m), 1.30(1H, d, J=12.5 Hz), 1.23(1H, m), 1.03(3H, d, J=6.7 Hz), 1.02(1H, m), 0.95(3H, d, J=6.7 Hz), 0.79(3H, d, J=6.7 Hz).

EXAMPLE 18
Preparation of 8a-[[[6-(benzoyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (23)

(Step 1) Preparation of 8a-[[[6-(acetyloxy)tetrahydro-7-hydroxy-2,5-methanofuro[2,3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (3)

1.00 g of compound (1) was dissolved in 40 ml of methanol and mixed with 760 mg of diphenyldiazomethane, and the reaction was conducted at room temperature for 13 hours under stirring. The reaction solution was concentrated in vacuo, charged onto a silica gel column (Kieselgel 60, Merck, 2.9φ×30 cm) and eluted with chloroform and then with chloroform-methanol (50:1). The fraction containing the desired product was concentrated in vacuo to give 1.205 g of compound (3) as a colorless powder.

Rf: 0.75 (Kieselgel 60F254, Merck, chloroform-methanol; 50:1).

FAB-MS(m/z): 699[M+H]$^+$.

$^1$H-NMR(δ ppm, 500 MHz, CDCl$_3$):9.73(1H, s), 7.26–7.44(10H, m), 6.96(1H, s), 6.09(1H, brd, J=3.7 Hz), 5.72(1H, brd, J=3.0 Hz), 4.71(2H, m), 4.39(1H, m), 4.13 (1H, d, J=9.8 Hz), 3.99(1H, d, J=9.8 Hz), 3.69(1H, brd, J=9.8 Hz), 2.82(1H, t, J=3.7 Hz), 2.46(1H, d, J=9.8 Hz), 2.25(1H, m), 2.16(3H, s), 1.82–1.96(5H, m), 1.58(3H, m), 1.25(1H, d, J=12.8 Hz), 0.98(3H, d, J=7.0 Hz), 0.93(2H, m), 0.73(3H, d, J=6.7 Hz), 0.26(3H, d, J=6.7 Hz).

(Step 2) Preparation of 8a-[[[6-(hydroxy)tetrahydro-7-hydroxy-2,5-methanofuro[2,3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (4)

650 mg of compound (3) was dissolved in 46 ml of methanol and stirred together with 13.9 ml of 0.1 N aqueous NaOH at room temperature for 2 hours. The reaction solution mixed with 24 ml of water and stirred at 4° C. for 2 hours. The reaction solution was filtered, and the recovered precipitate was washed with water and dried to give 464 mg of compound (4) as a colorless powder.

Rf: 0.28 (Kieselgel 60F254, Merck, chloroform-methanol; 50:1).

FAB-MS(m/z): 657[M+H]$^+$.

$^1$H-NMR(δ ppm, 500 MHz, CDCl$_3$):9.73(1H, s), 7.26–7.44(10H, m), 6.97(1H, s), 6.10(1H, brd, J=3.7 Hz), 5.70(1H, brd, J=3.0 Hz), 4.56(1H, m), 4.24(1H, m), 4.11 (1H, d, J=9.8 Hz), 4.05(1H, m), 4.02(1H, d, J=9.8 Hz), 3.70(1H, brd, J=9.8 Hz), 2.81(1H, t, J=3.7 Hz), 2.46(1H, d, J=9.8 Hz), 2.44(1H, d, J=10.1 Hz), 2.26(1H, m), 1.83–1.96 (5H, m), 1.58(3H, m), 1.25(1H, d, J=12.8 Hz), 1.00(3H, d, J=6.7 Hz), 0.93(2H, m), 0.74(3H, d, J=6.7 Hz), 0.27(3H, d, J=6.7 Hz).

(Step 3) Preparation of Compound (23)

40 mg of compound (4) was dissolved in 4 ml of dichloromethane and stirred together with 1.9 mg of sodium hydride at room temperature. After 0.5 hour 13.9 mg of benzoyl chloride was added, and after 2 hours and after 5 hours 0.9 mg of sodium hydride was added, while the reaction was conducted for 7 hours under stirring.

Then, the reaction solution was poured into 100 ml of 0.1 M sodium phosphate buffer pH 5.5 and extracted with 100 ml of ethyl acetate. The ethyl acetate extract was concentrated in vacuo, charged onto a silica gel column (Kieselgel 60, Merck, 1.5φ×30 cm) and eluted with chloroform-methanol (100:1). The fraction containing the desired product was concentrated in vacuo to give 19 mg of a residue. Then, the resulting residue was dissolved in 1 ml of ethyl acetate and stirred together with a catalytic amount of 10% palladium-carbon under a hydrogen atmosphere at room temperature for 4 hours. After the reaction, the reaction solution was filtered, and the filtrate was concentrated in vacuo, subjected to chromatography using a silica gel column (Kieselgel 60, Merck, 1.5φ×30 cm) and eluted with chloroform-methanol (20:1). The fraction containing the desired product was concentrated to dryness to give 11.7 mg of compound (23).

Rf: 0.43 (Kieselgel 60F254, Merck, chloroform-methanol; 50:1).

FAB-MS(m/z): 595[M+H]$^+$.

$^1$H-NMR(δ ppm, 500 MHz, CDCl$_3$):9.67(1H, s), 8.07 (2H, d, J=7.6 Hz), 7.63(1H, t, J=7.6 Hz), 7.50(2H, t, J=7.6 Hz), 6.08(1H, brd, J=3.7 Hz), 5.81(1H, brd, J=4.0 Hz), 4.94(1H, t, J=4.0 Hz), 4.89(1H, m), 4.54(1H, m), 4.04(1H, d, J=9.8 Hz), 3.96(1H, d, J=9.8 Hz), 3.82 (1H, brs), 2.79(1H, t, J=3.7 Hz), 2.31(1H, m), 1.94–2.12(5H, m), 1.85(1H, m), 1.76(2H, m), 1.29(1H, d, J=12.5 Hz), 1.23(1H, m), 1.02(1H, m), 1.00(3H, d, J=6.7 Hz), 0.94(3H, d, J=6.7 Hz), 0.79(3H, d, J=6.7 Hz).

EXAMPLE 19

Preparation of 8a-[[[6,7-di(benzoyloxy)tetrahydro-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (24)

In the first silica gel chromatography in Example 18, the fraction containing the desired compound eluted earlier than compound (23) was concentrated to give a residue. The resulting residue was dissolved in 1 ml of ethyl acetate and stirred together with a catalytic amount of 10% palladium-carbon under a hydrogen atmosphere at room temperature for 3 hours. After the reaction, the reaction solution was filtered, and the filtrate was concentrated in vacuo, subjected to silica gel column chromatography (Kieselgel 60, Merck, 1.5φ×30 cm) and eluted with chloroform-methanol (20:1). The fraction containing the desired product was concentrated to dryness to give 7.0 mg of compound (24).

Rf: 0.76 (Kieselgel 60F254, Merck, chloroform-methanol; 50:1).

FAB-MS(m/z): 699[M+H]$^+$.

$^1$H-NMR(δ ppm, 500 MHz, CDCl$_3$):9.59(1H, s), 8.15 (4H, m), 7.63(2H, m), 7.50(4H, m), 6.04(1H, brd, J=3.7 Hz), 5.96(1H, brd, J=3.0 Hz), 5.34(1H, brs), 5.02(1H, t, J=3.4 Hz), 4.96(1H, m), 4.74(1H, m), 4.08(1H, d, J=9.8 Hz), 3.92(1H, d, J=9.8 Hz), 2.61(1H, t, J=3.7 Hz), 2.27(1H, m), 1.70–2.00(6H, m), 1.63(1H, t, J=13.6 Hz), 1.38(1H, m), 1.16(2H, m), 0.97(3H, d, J=6.7 Hz), 0.91 (1H, m), 0.90(3H, d, J=6.7 Hz), 0.69(3H, d, J=7.0 Hz).

EXAMPLE 20

Preparation of 8a-[[[6-(Phenylacetyloxy)tetrahydro-7-hydroxy-2,5-methanofuro[2,3-d]-1,3-dioxol-2yl]oxy]methyl]-4-formyl-4,4a,5,6,7,7a,8,8a-octahydro-7-methyl-3-(1-methylethyl)-1,4-methano-s-indacene-3a(1H)-carboxylic acid (25)

50 mg of compound (4) was dissolved in 4 ml of dry dimethylformamide and stirred together with 5.5 mg of sodium hydride under cooling with ice. After 0.5 hour, 17.7 mg of phenylacetyl chloride was added, while the reaction was conducted for 4 hours under stirring.

Then, the reaction solution was poured into 100 ml of 0.1 M sodium phosphate buffer pH 5.5 and extracted with 100 ml of ethyl acetate. The ethyl acetate extract was concentrated in vacuo, charged onto a silica gel column (Kieselgel 60, Merck, 1.5φ×30 cm) and eluted with n-hexane-ethyl acetate (2:1). The fraction containing the desired product was concentrated in vacuo to give 18.3 mg of a residue.

Then, the resulting residue was dissolved in 1.5 ml of ethyl acetate and stirred together with a catalytic amount of 10% palladium-carbon under a hydrogen atmosphere at room temperature for 2 hours. After the reaction, the reaction solution was filtered, and the filtrate was concentrated in vacuo, subjected to silica gel column chromatography (Kieselgel 60, Merck, 1.5φ×30 cm) and eluted with chloroform-methanol (20:1). The fraction containing the desired product was concentrated to dryness to give 10.6 mg of compound (25).

Rf: 0.23 (Kieselgel 60F254, Merck, chloroform-methanol; 50:1).

FAB-MS(m/z): 609[M+H]$^+$.

$^1$H-NMR(δ ppm, 500 MHz, CDCl$_3$):9.69(1H, s), 7.26–7.36(5H, m), 6.10(1H, brd, J=3.7 Hz), 5.72(1H, brd, J=3.0 Hz), 4.76(1H, m), 4.70(1H, t, J=3.7 Hz), 4.37(1H, m), 4.00(1H, d, J=9.8 Hz), 3.96(1H, d, J=9.8 Hz), 3.73 (2H, s), 3.59(1H, brs), 2.78(1H, t, J=3.7 Hz), 2.34(1H, m), 1.74–2.10 (8H, m), 1.32(1H, d, J=12.5 Hz), 1.23(1H, m), 1.05(1H, m), 1.04(3H, d, J=6.7 Hz), 0.97(3H, d, J=6.7 Hz), 0.80(3H, d, J=6.7 Hz).

EXAMPLE 21

Preparation of 8a-[[[6-(3-phenylpropionyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (26)

50 mg of compound (4) was dissolved in 4 ml of dry dimethylformamide and stirred together with 5.5 mg of sodium hydride under cooling with ice. After 0.5 hour, 17.4 mg of cinnamoyl chloride was added, and the reaction was conducted for 4 hours under stirring. Then, the reaction solution was poured into 100 ml of 0.1 M sodium phosphate buffer pH 5.5 and extracted with 100 mg of ethyl acetate. The ethyl acetate extract was concentrated in vacuo, charged onto a silica gel column (Kieselgel 60, Merck, 1.5φ×30 cm) and eluted with n-hexane-ethyl acetate (2:1). The fraction containing the desired product was concentrated in vacuo to give 18 mg of a residue.

Then, the resulting residue was dissolved in 1 ml of ethyl acetate and stirred together with a catalytic amount of 10% palladium-carbon under a hydrogen atmosphere at room temperature for 2 hours. After the reaction, the reaction solution was filtered, and the filtrate was concentrated in vacuo, subjected to silica gel column chromatography (Kieselgel 60, Merck, 1.5φ×30 cm) and eluted with 200 ml of chloroform-methanol (40:1) and 200 ml of chloroform-methanol (20:1) successively. The fraction containing the desired product was concentrated to dryness to give 3.0 mg of compound (26).

Rf: 0.45 (Kieselgel 60F254, Merck, chloroform-methanol; 20:1).

FAB-MS(m/z): 623[M+H]$^+$.

$^1$H-NMR(δ ppm, 500 MHz, CDCl$_3$):9.65(1H, s), 7.20–7.32(5H, m), 6.10(1H, brd, J=3.7 Hz), 5.72(1H, brd, J=3.0 Hz), 4.72(2H, m), 4.34(1H, m), 4.03(1H, d, J=9.8 Hz), 3.94(1H, d, J=9.8 Hz), 3.57(1H, brs), 2.97(2H, t, J=7.4 Hz), 2.70–2.80(3H, m), 2.34(1H, m), 1.70–2.10(8H, m), 1.20–1.30(2H, m), 1.02(3H, d, J=6.7 Hz), 1.00(1H, m), 0.97(3H, d, J=6.7 Hz), 0.79(3H, d, J=6.7 Hz).

EXAMPLE 22

Preparation of 8a-[[[6-(ethoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (29)

(Step 1) Preparation of 8a-[[[6-(acetyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7- methyl-3-(1-methylethyl)-1,4-methano-s-indacene-3a(1H)-carboxylic acid diphenylmethyl ester (5)

100 mg of compound (3) was dissolved in 0.7 ml of anhydrous dichloromethane and stirred together with 70 mg of dimethylaminopyridine and 49 μl of t-butyldimethylsilyl trifluoromethanesulfonate for 1 hour under cooling with ice. The reaction solution was concentrated in vacuo, dissolved in methanol, charged onto a silica gel column (Kieselgel 60, Merck, 1.5φ×22 cm) and eluted with n-hexane-ethyl acetate (4:1). The fraction containing the desired product was concentrated in vacuo to give 99 mg of compound (5) as a colorless oily substance.

Rf: 0.62 (Kieselgel 60F254, Merck, n-hexane-ethyl acetate; 2:1).

FAB-MS(m/z): 813[M+H]$^+$.

(Step 2) Preparation of 8a-[[[6-(hydroxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (6)

90 mg of compound (5) was dissolved in 2.2 ml of methanol and stirred together with 121 μl of 1N NaOH for 2 hours under cooling with ice. After addition of water, the reaction solution was extracted with ethyl acetate, and the ethyl acetate extract was dried over anhydrous sodium sulfate and concentrated in vacuo to dryness to give 66 mg of compound (6) as a colorless powder.

Rf: 0.38 (Kieselgel 60F254, Merck, n-hexane-ethyl acetate; 2:1).

FAB-MS(m/z): 793[M+Na]$^+$.

$^1$H-NMR(δ ppm, 500 MHz, CDCl$_3$):9.74(1H, s), 7.25–7.43(10H, m), 6.97(1H, s), 6.09(1H, brd, J=3.7 Hz), 5.75(1H, brd, J=3.0 Hz), 4.40(1H, m), 4.19(1H, d, J=9.8 Hz), 4.12(1H, m), 4.01(1H, m), 3.97(1H, d, J=9.8 Hz), 3.76(1H, brs), 2.80(1H, t, J=3.7 Hz), 2.45(1H, d, J=10.4 Hz), 2.23(1H, m), 1.99(1H, m), 1.82–1.95(5H, m), 1.56(2H, m), 1.25(1H, d, J=12.5 Hz), 0.98(3H, d, J=6.7 Hz), 0.92(9H, s), 0.88–0.96(2H, m), 0.73(3H, d, J=6.7 Hz), 0.26(3H, d, J=6.7 Hz), 0.14(3H, s), 0.13(3H, s).

(Step 3) Preparation of 8a-[[[6-(ethoxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (27)

48.0 mg of compound (6) was dissolved in 0.4 ml of dry dimethylformamide, and about 5 mg of sodium hydride was added under cooling with ice. After 15 minutes, 19 μl of ethyl bromide was added, and the reaction solution was stirred under cooling with ice. After 50 minutes, the reaction solution was brought back to room temperature and allowed to react for another 90 minutes under stirring. Then, the reaction solution was charged onto a silica gel column (Kieselgel 60, Merck, 1.0φ×25 cm) and eluted with n-hexane-ethyl acetate (4:1) to give 36.8 mg of compound (27) as a colorless oily substance.

Rf: 0.57 (Kieselgel 60F254, Merck, n-hexane-ethyl acetate; 2:1).

FAB-MS(m/z): 799[M+H]$^+$.

(Step 4) Preparation of 8a-[[[6-(ethoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (28)

Compound (27) was mixed with in 70 μl of 1M tetrabutylammonium fluoride-tetrahydrofuran solution and stirred at room temperature. After 80 minutes, the reaction solution was mixed with 15 ml of ethyl acetate and washed with 10 ml of sodium phosphate buffer (10 mM, pH 5.97) and then with 10 ml of water twice. After the washing, the ethyl acetate layer was dried over anhydrous sodium sulfate, filtered for removal of solids and concentrated in vacuo to give a crude reaction product. The reaction product was further subjected to silica gel column chromatography (Kieselgel 60, Merck, 1.5φ×15 cm) and eluted with n-hexane-ethyl acetate (3:1) to give 21.2 mg of compound (28) as a colorless oily substance.

Rf: 0.41 (Kieselgel 60F254, Merck, n-hexane-ethyl acetate; 2:1).

FAB-MS(m/z): 685[M+H]$^+$.

(Step 5) Preparation of Compound (29)

21.2 mg of compound (28) was dissolved in 6 ml of ethyl acetate and stirred together with a catalytic amount of 10% palladium-carbon under a hydrogen atmosphere at room temperature for 50 minutes. The reaction solution was filtered, and the filtrate was concentrated in vacuo. The reaction product was dissolved in 4 ml of methanol and washed with 4 ml of n-hexane twice. The methanol layer was concentrated in vacuo to give 10.0 mg of compound (29) as a colorless oily substance.

Rf: 0.40 (Kieselgel 60F254, Merck, chloroform-methanol; 10:1).

FAB-MS(m/z): 519[M+H]$^+$.

$^1$H-NMR(δ ppm, 300 MHz, CDCl$_3$):9.67(1H, s), 6.10 (1H, d, J=3.7 Hz), 5.69(1H, d, J=3.7 Hz), 4.54(1H, m), 4.32(1H, m), 4.03(1H, d, J=8.3 Hz), 3.95(1H, d, J=8.3 Hz), 3.53–3.79(4H, m), 2.82(1H, t, J=3.4 Hz), 2.32(1H, m), 1.79–2.13(6H, m), 1.67–1.79(2H, m), 1.14–1.27 (2H, m), 1.26(3H, t, J=7.5 Hz), 1.02(1H, m), 1.02(3H, d, J=6.8 Hz), 0.94(3H, d, J=6.8 Hz), 0.78(3H, d, J=6.8 Hz).

EXAMPLE 23

Preparation of 8a-[[[6-(propoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (32)

(Step 1) Preparation of 8a-[[[6-(propoxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid dimethylphenylmethyl ester (30)

50 mg of compound (6) was dissolved in 1.0 ml of dry dimethylformamide under a nitrogen atmosphere and mixed with about 4 mg of sodium hydride under cooling with ice. After 30 minutes, 56.3 μl of 1-chloropropane was added, and the reaction solution was stirred at room temperature for 3 hours. Then, the reaction solution was charged onto a silica gel column (Kieselgel 60, Merck, 1.0φ×30 cm) and eluted with n-hexane-ethyl acetate (4:1). The fraction containing the desired product was concentrated to dryness to give 21.6 mg of compound (30).

Rf: 0.70 (Kieselgel 60F254, Merck, n-hexane-ethyl acetate; 2:1).

FAB-MS(m/z): 813[M+H]$^+$.

(Step 2) Preparation of 8a-[[[6-(propoxy)tetrahydro-7-hydroxy-2,5-methanofuro[2,3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid dimethylphenylmethyl ester (31)

21 mg of compound (30) was mixed with 53.2 μl of 1M tetrabutylammonium fluoride-tetrahydrofuran solution, and the reaction was conducted at room temperature under stirring for 2 hours. The reaction solution was charged onto a silica gel column (Kieselgel 60, Merck, 1.0φ×30 cm) and eluted with n-hexane-ethyl acetate (2:1). The fraction containing the desired product was concentrated to dryness to give 16 mg of compound (31).

Rf: 0.32 (Kieselgel 60F254, Merck, n-hexane-ethyl acetate; 2:1).

FAB-MS(m/z): 699[M+H]$^+$.

(Step 3) Preparation of Compound (32)

13 mg of compound (31) was dissolved in 2 ml of ethyl acetate and allowed to react in the presence of a catalytic amount of 10% palladium-carbon under stirring under a hydrogen atmosphere at room temperature for 1 hour. The reaction solution was filtered, and the filtrate was concentrated in vacuo. The reaction product was charged onto a silica gel column (Kieselgel 60, Merck, 1.0φ×30 cm) and eluted with chloroform-methanol (20:1). The fraction containing the desired product was concentrated to dryness to give 9.0 mg of compound (32).

Rf: 0.39 (Kieselgel 60F254, Merck, chloroform-methanol; 50:1).

FAB-MS(m/z): 533[M+H]$^+$.

$^1$H-NMR(δ ppm, 500 MHz, CDCl$_3$):9.68(1H, s), 6.10 (1H, brd, J=4.0 Hz), 5.70(1H, brd, J=2.8 Hz), 4.55(1H, m), 4.31(1H, m), 4.03(1H, d, J=9.8 Hz), 3.98(1H, d, J=9.8 Hz), 3.74(1H, d, J=0.8 Hz), 3.72(1H, t, J=3.7 Hz), 3.60(1H, m), 3.49(1H, m), 2.81(1H, t, J=4.0 Hz), 2.33 (1H, m), 1.90–2.10 (5H, m), 1.87(1H, m), 1.76(2H, m), 1.66(2H, m), 1.29(1H, d, J=13.1 Hz), 1.22(1H, m), 1.02(3H, d, J=6.8 Hz), 1.00(1H, m), 0.95(3H, t, J=7.3 Hz), 0.95(3H, d, J=6.8 Hz), 0.79(3H, d, J=6.8 Hz).

EXAMPLE 24

Preparation of 8a-[[[6-(isopropoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (35)

(Step 1) Preparation of 8a-[[[6-(isopropoxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (33)

50 mg of compound (6) was dissolved in 1.0 ml of dry dimethylformamide under a nitrogen atmosphere and mixed with about 3 mg of sodium hydride under cooling with ice. After 30 minutes, 12.2 μl of 2-bromopropane was added, and the reaction solution was stirred at room temperature. The reaction solution was allowed to react for 63 hours, while about 3 mg of sodium hydride and 12.2 μl of 2-bromopropane were added after 40 hours and further after 46 hours. Then, the reaction solution was charged onto a silica gel column (Kieselgel 60, Merck, 1.0φ×30 cm) and eluted with n-hexane-ethyl acetate (2:1). The fraction containing the desired product was concentrated to dryness to give 13.6 mg of compound (33).

Rf: 0.78 (Kieselgel 60F254, Merck, n-hexane-ethyl acetate; 2:1).

FAB-MS(m/z): 835[M+Na]$^+$.

(Step 2) Preparation of 8a-[[[6-(isopropoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (34)

13 mg of compound (33) was mixed with 200 μl of tetrahydrofuran and 14.8 μl of 1M tetrabutylammonium fluoride-tetrahydrofuran solution, and the reaction was conducted at room temperature under stirring for 15 hours. The reaction solution was charged onto a silica gel column (Kieselgel 60, Merck, 1.0φ×30 cm) and eluted with n-hexane-ethyl acetate (2:1). The fraction containing the desired product was concentrated to dryness to give 9.0 mg of compound (34).

Rf: 0.30 (Kieselgel 60F254, Merck, n-hexane-ethyl acetate; 2:1).

FAB-MS(m/z): 699[M+H]$^+$.

(Step 3) Preparation of Compound (35)

9 mg of compound (34) was dissolved in 2 ml of ethyl acetate and allowed to react in the presence of a catalytic amount of 10% palladium-carbon under stirring under a hydrogen atmosphere at room temperature for 2 hours. The reaction solution was filtered, and the filtrate was concentrated in vacuo. The reaction product was charged onto a silica gel column (Kieselgel 60, Merck, 1.0φ×30 cm) and eluted with chloroform-methanol (30:1). The fraction containing the desired product was concentrated to dryness to give 6.8 mg of compound (35).

Rf: 0.39 (Kieselgel 60F254, Merck, chloroform-methanol; 50:1).

FAB-MS(m/z): 533[M+H]$^+$.

$^1$H-NMR(δ ppm, 500 MHz, CDCl$_3$):9.68(1H, s), 6.11 (1H, brd, J=3.7 Hz), 5.70(1H, brd, J=4.0 Hz), 4.51(1H, m), 4.26(1H, m), 4.04(1H, d, J=9.8 Hz), 3.96(1H, d, J=9.8 Hz), 3.77–3.84(2H, m), 3.75(1H, brs), 2.81(1H, t, J=3.7 Hz), 2.32(1H, m), 1.93–2.12(5H, m), 1.87(1H, m), 1.76(2H, m), 1.29(1H, d, J=12.5 Hz), 1.24(3H, d, J=6.3 Hz), 1.23(3H, d, J=6.3 Hz), 1.23(1H, m), 1.03(3H, d, J=7.0 Hz), 1.02(1H, m), 0.95(3H, d, J=6.7 Hz), 0.79 (3H, d, J=6.7 Hz).

EXAMPLE 25

Preparation of 8a-[[[6-(butoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1 -methylethyl)-1,4-methano-s-indacene-3a(1H)-carboxylic acid (38)

(Step 1) Preparation of 8a-[[[6-(butoxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (36)

32 mg of compound (6) was dissolved in 0.4 ml of dry dimethylformamide under a nitrogen atmosphere and mixed with about 5 mg of sodium hydride under cooling with ice. After 15 minutes, 25.6 μl of butyl bromide was added, and the reaction solution was stirred for 50 minutes. The reaction solution was allowed to react at room temperature further for 13 hours under stirring. Then, the reaction solution was charged onto a silica gel column (Kieselgel 60, Merck, 1.0φ×22 cm) and eluted with n-hexane-ethyl acetate (4:1) to give 26 mg of compound (36) as a colorless oily substance.

Rf: 0.72 (Kieselgel 60F254, Merck, n-hexane-ethyl acetate; 2:1).

FAB-MS(m/z): 849[M+Na]$^+$.

(Step 2) Preparation of 8a-[[[6-(butoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (37)

20 mg of compound (36) was stirred together with 242 μl of dry tetrahydrofuran and 36 μl of 1M tetrabutylammonium fluoride-tetrahydrofuran solution at room temperature for 1 hour. The reaction solution was concentrated in vacuo to give the crude reaction product. It was charged onto a silica gel column (Kieselgel 60, Merck, 1.5φ×15 cm) and eluted with n-hexane-ethyl acetate (3:1) to give 20.5 mg of compound (37) as a colorless oily substance.

Rf: 0.38 (Kieselgel 60F254, Merck, n-hexane-ethyl acetate; 2:1).

FAB-MS(m/z): 713[M+H]$^+$.

(Step 3) Preparation of Compound (38)

20.5 mg of compound (37) was dissolved in 1 ml of ethyl acetate and allowed to react in the presence of a catalytic amount of 10% palladium-carbon under stirring under a hydrogen atmosphere at room temperature for 1 hour. The reaction solution was filtered, and the filtrate was concentrated in vacuo. The reaction product was charged onto a silica gel column (Kieselgel 60, Merck, 1.0φ×22 cm) and eluted with n-hexane-ethyl acetate (1:1) to give 8.8 mg of compound (38) as a colorless oily substance.

Rf: 0.39 (Kieselgel 60F254, Merck, ethyl acetate).

FAB-MS(m/z): 569[M+Na]$^+$.

$^1$H-NMR(δ ppm, 500 MHz, CDCl$_3$):9.68(1H, s), 6.11 (1H, brd, J=3.7 Hz), 5.70(1H, brd, J=2.8 Hz), 4.55(1H, m), 4.30(1H, m), 4.04(1H, d, J=9.8 Hz), 3.97(1H, d, J=9.8 Hz), 3.73(1H, brs), 3.72(1H, t, J=4.0 Hz), 3.64(1H, m), 3.53(1H, m), 2.81(1H, t, J=3.7 Hz), 2.33(1H, m), 1.94–2.12(5H, m), 1.86(1H, m), 1.76(2H, m), 1.62(2H, m), 1.40(2H, m), 1.29 (1H, d, J=12.5 Hz), 1.24(1H, m), 1.03(1H, m), 1.03(3H, d, J=6.7 Hz), 0.96(3H, d, J=6.7 Hz), 0.94(3H, t, J=7.3 Hz), 0.79(3H, d, J=6.7 Hz).

EXAMPLE 26

Preparation of 8a-[[[6-(pentyloxy)tetrahydro-7-hydroxy-2, 5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (41)

(Step 1) Preparation of 8a-[[[6-(pentyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (39)

50 mg of compound (6) was dissolved in 0.5 ml of dry dimethylformamide under a nitrogen atmosphere and mixed with about 5 mg of sodium hydride under cooling with ice. After 30 minutes, 78.7 μl of 1-chloropentane was added, and the reaction solution was stirred at room temperature for 4 hours. Then, the reaction solution was charged onto a silica gel column (Kieselgel 60, Merck, 1.0φ×30 cm) and eluted with n-hexane-ethyl acetate (5:1). The fraction containing the desired product was concentrated to dryness to give 22.0 mg of compound (38).

Rf: 0.79 (Kieselgel 60F254, Merck, n-hexane-ethyl acetate; 2:1).

FAB-MS(m/z): 841[M+H]$^+$.

(Step 2) Preparation of 8a-[[[6-(pentyloxy)tetrahydro-7-hydroxy-2,5-methanofuro[2,3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (40)

22 mg of compound (39) was mixed with 500 μl of tetrahydrofuran and 52.4 μl of 1M tetrabutylammonium fluoride-tetrahydrofuran solution, and the reaction was conducted at room temperature under stirring for 2 hours.

The reaction solution was charged onto a silica gel column (Kieselgel 60, Merck, 1.0φ×30 cm) and eluted with n-hexane-ethyl acetate (3:1). The fraction containing the desired product was concentrated to dryness to give 16.6 mg of compound (40).

Rf: 0.42 (Kieselgel 60F254, Merck, n-hexane-ethyl acetate; 2:1).

FAB-MS(m/z): 727[M+H]$^+$.

(Step 3) Preparation of Compound (41)

15 mg of compound (40) was dissolved in 2 ml of ethyl acetate and allowed to react in the presence of a catalytic amount of 10% palladium-carbon under stirring under a hydrogen atmosphere at room temperature for 1 hour. The reaction solution was filtered, and the filtrate was concentrated in vacuo. The reaction product was charged onto a silica gel column (Kieselgel 60, Merck, 1.0φ×30 cm) and eluted with chloroform-methanol (40:1). The fraction containing the desired product was concentrated to dryness to give 11.5 mg of compound (41).

Rf: 0.30 (Kieselgel 60F254, Merck, chloroform-methanol; 20:1).

FAB-MS(m/z): 561[M+H]$^+$.

$^1$H-NMR(δ ppm, 400 MHz, CDCl$_3$):9.67(1H, s), 6.11(1H, dd, J=3.4, 1.0 Hz), 5.70(1H, dd, J=3.4, 1.0 Hz), 4.55 (1H, m), 4.31(1H, m), 4.04(1H, d, J=9.8 Hz), 3.97(1H, d, J=9.8 Hz), 3.71–3.74(2H, m), 3.63(1H, m), 3.52(1H, m), 2.81(1H, t, J=3.4 Hz), 2.33(1H, m), 1.94–2.11(5H, m), 1.86(1H, m), 1.72–1.81(2H, m), 1.64(2H, m), 1.18–1.38(6H, m), 1.02(3H, d, J=6.8 Hz), 1.01(1H, m), 0.95(3H, d, J=6.3 Hz), 0.91(3H, t, J=6.8 Hz), 0.79(3H, d, J=6.8 Hz).

EXAMPLE 27

Preparation of 8a-[[[6-(isopentyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (44)

(Step 1) Preparation of 8a-[[[6-(3-methyl-2-butenyloxy) tetrahydro-7-t-butyldimethylsilyloxy-2,5-methanofuro[2,3-d]-1,3-dioxol-2-yl]oxy]methyl]-4-formyl-4,4a,5,6,7,7a,8, 8a-octahydro-7-methyl-3-(1-methylethyl)-1,4-methano-s-indacene-3a(1H)-carboxylic acid diphenylmethyl ester (42)

50 mg of compound (6) was dissolved in 0.4 ml of dry dimethylformamide under a nitrogen atmosphere and mixed with about 5 mg of sodium hydride under cooling with ice. After 15 minutes, 37.4 ml of 4-bromo-2-methyl2-butene was added, and the reaction solution was stirred under cooling with ice for 50 minutes. The reaction solution was allowed to react at room temperature for another 20 minutes under stirring. Then, the reaction solution was charged onto a silica gel column (Kieselgel 60, Merck, 1.5φ×19 cm) and eluted with n-hexane-ethyl acetate (10:1) to give 34.4 mg of compound (42) as a colorless oily substance.

Rf: 0.72 (Kieselgel 60F254, Merck, n-hexane-ethyl acetate; 2:1).

FAB-MS(m/z): 861[M+Na]$^+$.

(Step 2) Preparation of 8a-[[[6-(3-methyl-2-butenyloxy) tetrahydro-7-hydroxy-2,5-methanofuro[2,3-d]- 1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (43)

31 mg of compound (42) was stirred together with 1.23 ml of dry tetrahydrofuran and 55.3 μl of 1M tetrabutylammonium fluoride-tetrahydrofuran solution at room temperature for 3 hours. The reaction solution was concentrated in vacuo to give the crude reaction product. It was charged onto a silica gel column (Kieselgel 60, Merck, 1.0φ×20 cm) and eluted with n-hexane-ethyl acetate (4:1) to give 31.7 mg of compound (43) as a colorless oily substance.

Rf: 0.36 (Kieselgel 60F254, Merck, n-hexane-ethyl acetate; 2:1).

FAB-MS(m/z): 725[M+H]$^+$.

(Step 3) Preparation of Compound (44)

30 mg of compound (43) was dissolved in 4.3 ml of ethyl acetate and allowed to react in the presence of a catalytic amount of 10% palladium-carbon under stirring under a hydrogen atmosphere at room temperature for 50 minutes. The reaction solution was filtered, and the filtrate was concentrated in vacuo. The reaction product was charged onto a silica gel column (Kieselgel 60, Merck, 1.0φ×21 cm) and eluted with n-hexane-ethyl acetate (3:1) to give 16.5 mg of compound (44) as a colorless oily substance.

Rf: 0.12 (Kieselgel 60F254, Merck, n-hexane-ethyl acetate; 2:1).

FAB-MS(m/z): 561[M+H]$^+$.

$^1$H-NMR($\delta$ ppm, 500 MHz, CDCl$_3$):9.68(1H, s), 6.11 (1H, brd, J=3.7 Hz), 5.70(1H, brd, J=3.0 Hz), 4.56(1H, m), 4.30(1H, m), 4.02(1H, d, J=9.8 Hz), 3.98(1H, d, J=9.8 Hz), 3.73(1H, brs), 3.72(1H, t, J=4.3 Hz), 3.66(1H, m), 3.55(1H, m), 2.81(1H, t, J=3.7 Hz), 2.32(1H, m), 1.93–2.10(5H, m), 1.86(1H, m), 1.75(3H, m), 1.53(2H, m), 1.29(1H, d, J=12.5 Hz), 1.23(1H, m), 1.03(3H, d, J=6.7 Hz), 1.02(1H, m), 0.95(3H, d, J=6.7 Hz), 0.92(6H, d, J=6.4 Hz), 0.79(3H, d, J=6.7 Hz).

EXAMPLE 28

Preparation of 8a-[[[6-(hexyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (47)

(Step 1) Preparation of 8a-[[[6-(hexyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (45)

100.0 mg of compound (6) was dissolved in 0.8 ml of dry dimethylformamide under a nitrogen atmosphere and mixed with about 10 mg of sodium hydride under cooling with ice. After 15 minutes, 44 $\mu$l of hexyl chloride was added, and the reaction solution was stirred under cooling with ice for 2 hours. The reaction solution was allowed to react at room temperature for another 90 minutes under stirring. Then, the reaction solution was charged onto a silica gel column (Kieselgel 60, Merck, 1.0$\phi$×21 cm) and eluted with n-hexane-ethyl acetate (4:1) to give 18.7 mg of compound (45) as a colorless oily substance.

Rf: 0.77 (Kieselgel 60F254, Merck, n-hexane-ethyl acetate; 2:1).

FAB-MS(m/z): 877[M+Na]$^+$.

(Step 2) Preparation of 8a-[[[6-(hexyloxy)tetrahydro-7-hydroxy-2,5-methanofuro[2, 3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (46)

18.7 mg of compound (45) was stirred together with 218 $\mu$l of dry tetrahydrofuran and 32.7 $\mu$l of 1M tetrabutylammonium fluoride-tetrahydrofuran solution at room temperature for 4 hours. The reaction solution was concentrated in vacuo to give the crude reaction product. It was charged onto a silica gel column (Kieselgel 60, Merck, 1.0$\phi$×20 cm) and eluted with n-hexane-ethyl acetate (8:1) to give 16.3 mg of compound (46) as a colorless oily substance.

Rf: 0.43 (Kieselgel 60F254, Merck, n-hexane-ethyl acetate; 2:1).

FAB-MS(m/z): 741[M+H]$^+$.

(Step 3) Preparation of Compound (47)

14.1 mg of compound (46) was dissolved in 1.9 ml of ethyl acetate and allowed to react in the presence of a catalytic amount of 10% palladium-carbon under stirring under a hydrogen atmosphere at room temperature for 3 hours. The reaction solution was filtered, and the filtrate was concentrated in vacuo. The reaction product was charged onto a silica gel column (Kieselgel 60, Merck, 1.5$\phi$×15 cm) and eluted with n-hexane-ethyl acetate (3:1) to give 6.0 mg of compound (47) as a colorless oily substance.

Rf: 0.37 (Kieselgel 60F254, Merck, hexane-ethyl acetate; 1:1).

FAB-MS(m/z): 575[M+H]$^+$.

$^1$H-NMR($\delta$ ppm, 500 MHz, CDCl$_3$):9.67(1H, s), 6.10 (1H, brd, J=3.7 Hz), 5.69(1H, brd, J=3.0 Hz), 4.55(1H, m), 4.30(1H, m), 4.06(1H, d, J=9.8 Hz), 3.96(1H, d, J=9.8 Hz), 3.73(1H, d, J=1.5 Hz), 3.72(1H, t, J=3.7 Hz), 3.63(1H, m), 3.52(1H, m), 2.79(1H, t, J=3.7 Hz), 2.33 (1H, m), 1.94–2.12 (5H, m), 1.85(1H, m), 1.78(2H, m), 1.63(2H, m), 1.20–1.40 (8H, m), 1.04(1H, m), 1.02(3H, d, J=6.7 Hz), 0.96(3H, d, J=6.7 Hz), 0.90(3H, t, J=7.3 Hz), 0.79(3H, d, J=6.7 Hz).

EXAMPLE 29

Preparation of 8a-[[[6-(decyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1 -methylethyl)-1,4-methano-s-indacene-3a(1H)-carboxylic acid (50)

(Step 1) Preparation of 8a-[[[6-(decyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (48)

62.8 mg of compound (6) was dissolved in 0.4 ml of dry dimethylformamide under a nitrogen atmosphere and mixed with about 7 mg of sodium hydride under cooling with ice. After 15 minutes, 80 $\mu$l of decyl bromide was added, and the reaction solution was allowed to react at room temperature under stirring for another 18 hours. Then, the reaction solution was charged onto a silica gel column (Kieselgel 60, Merck, 1.0$\phi$×20 cm) and eluted with n-hexane-ethyl acetate (4:1) to give 85.7 mg of compound (48) as a colorless oily substance.

Rf: 0.84 (Kieselgel 60F254, Merck, n-hexane-ethyl acetate; 2:1).

FAB-MS(m/z): 933[M+Na]$^+$.

(Step 2) Preparation of 8a-[[[6-(decyloxy)tetrahydro-7-hydroxy-2,5-methanofuro[2,3-d]-1,3-dioxol-2-yl]oxy] methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (49)

85.7 mg of compound (48) was stirred together with 120 $\mu$l of 1M tetrabutylammonium fluoride-tetrahydrofuran solution at room temperature for 45 minutes.

After addition of 50 ml of ethyl acetate, the reaction solution was washed with 40 ml of sodium phosphate buffer (10 mM, pH 5.97) and then 40 ml of water twice. The washed ethyl acetate layer was dried over anhydrous sodium sulfate and filtered. The resulting ethyl acetate layer was concentrated in vacuo to give the crude reaction product.

The reaction product was charged onto a silica gel column (Kieselgel 60, Merck, 1.5$\phi$×14 cm) and eluted with n-hexane-ethyl acetate (4:1) to give 44.3 mg of compound (49) as a colorless oily substance.

Rf: 0.66 (Kieselgel 60F254, Merck, n-hexane-ethyl acetate; 2:1).

FAB-MS(m/z): 797[M+H]$^+$.

(Step 3) Preparation of Compound (50)

44.3 mg of compound (49) was dissolved in 5 ml of ethyl acetate and allowed to react in the presence of a catalytic amount of 10% palladium-carbon under stirring under a hydrogen atmosphere at room temperature for 70 minutes. The reaction solution was filtered, and the filtrate was concentrated in vacuo to give the crude reaction product. The crude reaction product was charged onto a silica gel column (Kieselgel 60, Merck, 1.5$\phi$×15 cm) and eluted with 150 ml of n-hexane-ethyl acetate (2:1), 200 ml of n-hexane-ethyl acetate (1:3) and finally chloroform-methanol (10:1) to give 19.8 mg of compound (50) as a colorless oily substance.

Rf: 0.15 (Kieselgel 60F254, Merck, n-hexane-ethyl acetate; 2:1).

FAB-MS(m/z): 631[M+H]$^+$.

$^1$H-NMR($\delta$ ppm, 500 MHz, CDCl$_3$):9.65(1H, s), 6.10 (1H, brd, J=3.7 Hz), 5.70(1H, brd, J=4.0 Hz), 4.55(1H, m), 4.31(1H, m), 4.04(1H, d, J=9.8 Hz), 4.97(1H, d, J=9.8 Hz), 3.74(1H, brs), 3.72(1H, t, J=3.7 Hz), 3.63(1H, m), 3.52(1H, m), 2.79(1H, brt, J=4.0 Hz), 2.34(1H, m), 1.84–2.12(6H, m), 1.75(2H, m), 1.63(2H, m), 1.18–1.38(16H, m), 1.02(3H, d, J=6.7 Hz), 1.01(1H, m), 0.96 (3H, d, J=6.7 Hz), 0.88(3H, t, J=7.3 Hz), 0.79(3H, d, J=6.7 Hz).

EXAMPLE 30

Preparation of 8a-[[[6-(cetyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (53)

(Step 1) Preparation of 8a-[[[6-(cetyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (51)

115 mg of compound (6) was dissolved in 1.5 ml of dry dimethylformamide under a nitrogen atmosphere and mixed with 13.8 mg of sodium hydride under cooling with ice. After 30 minutes, 225 μl of cetyl chloride was added, and the reaction solution was stirred under cooling with ice. After 30 minutes, the reaction solution was brought back to room temperature and allowed to react for another 90 minutes under stirring.

Then, the reaction solution was charged onto a silica gel column (Kieselgel 60, Merck, 1.5φ×22 cm) and eluted with n-hexane-ethyl acetate (8:1) to give 43.3 mg of compound (51) as a colorless oily substance.

Rf: 0.80 (Kieselgel 60F254, Merck, n-hexane-ethyl acetate; 2:1).

FAB-MS(m/z): 1017[M+Na]$^+$.

(Step 2) Preparation of 8a-[[[6-(cetyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (52)

43.3 mg of compound (51) was stirred together with 435 μl of dry tetrahydrofuran and 65.3 μl of 1M tetrabutylammonium fluoride-tetrahydrofuran solution at room temperature for 1 hour. The reaction solution was concentrated in vacuo to give the crude product. The reaction product was charged onto a silica gel column (Kieselgel 60, Merck, 1.0φ×20 cm) and eluted with n-hexane-ethyl acetate (8:1) to give 22.5 mg of compound (52) as a colorless oily substance.

Rf: 0.53 (Kieselgel 60F254, Merck, n-hexane-ethyl acetate; 2:1).

FAB-MS(m/z): 903[M+Na]$^+$.

(Step 3) Preparation of Compound (53)

25.0 mg of compound (52) was dissolved in 2.89 ml of ethyl acetate and allowed to react in the presence of a catalytic amount of 10% palladium-carbon under stirring under a hydrogen atmosphere at room temperature for 1 hour. The reaction solution was filtered, and the filtrate was concentrated in vacuo. The reaction product was charged onto a silica gel column (Kieselgel 60, Merck, 1.0φ×21 cm) and eluted with n-hexane-chloroform (2:1) to give 12.3 mg of compound (53) as a colorless oily substance.

Rf: 0.15 (Kieselgel 60F254, Merck, n-hexane-ethyl acetate; 2:1).

FAB-MS(m/z): 737[M+Na]$^+$.

$^1$H-NMR(δ ppm, 400 MHz, CDCl$_3$):9.67(1H, s), 6.10 (1H, dd, J=3.4, 1.0 Hz), 5.70(1H, dd, J=3.4, 1.5 Hz), 4.55(1H, m), 4.30(1H, m), 4.03(1H, d, J=9.8 Hz), 3.96 (1H, d, J=9.8 Hz), 3.70–3.74(2H, m), 3.63(1H, m), 3.52(1H, m), 2.81(1H, t, J=3.4 Hz), 2.32(1H, m), 1.92–2.12(5H, m), 1.87(1H, m), 1.72–1.80(2H, m), 1.62 (2H, m), 1.17–1.39 (28H, m), 1.02(3H, d, J=6.8 Hz), 1.00(1H, m), 0.95(3H, d, J=6.8 Hz), 0.88(3H, t, J=6.8 Hz), 0.78(3H, d, J=6.8 Hz).

EXAMPLE 31

Preparation of 8a-[[[6-(2-(N-piperidino)ethoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (56)

(Step 1) Preparation of 8a-[[[6-(2-(N-piperidino)ethoxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (54)

67.6 mg of compound (6) was dissolved in 0.2 ml of dry dimethylformamide under a nitrogen atmosphere and mixed with about 20 mg of sodium hydride under cooling with ice. After 15 minutes, 57 mg of 1-(2-chloroethyl)piperidine hydrochloride suspended in 1 ml of dimethylformamide was added, and the reaction solution was allowed to react at room temperature under stirring for 66 hours.

Then, the reaction solution was charged onto a silica gel column (Kieselgel 60, Merck, 1.0φ×30 cm) and eluted with 225 ml of n-hexane-ethyl acetate (2:1) and chloroform-methanol (10:1). The fraction containing the desired product was concentrated in vacuo. The concentrate was dissolved in 100 ml of ethyl acetate and washed with 100 ml of water four times. The ethyl acetate layer was concentrated to give 33.0 mg of compound (54) as a colorless oily substance.

Rf: 0.23 (Kieselgel 60F254, Merck, chloroform-methanol; 10:1).

FAB-MS(m/z): 882[M+H]$^+$.

(Step 2) Preparation of 8a-[[[6-(2-(N-piperidino)ethoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (55)

33.0 mg of compound (54) was stirred together with 60 μl of 1M tetrabutylammonium fluoride-tetrahydrofuran solution at room temperature for 45 minutes.

The reaction solution was charged onto a silica gel column (Kieselgel 60, Merck, 1.5φ×15 cm) and eluted with 25 ml of chloroform and then chloroform-methanol (5:1) to give 26.7 mg of compound (55) as a colorless oily substance.

Rf: 0.28 (Kieselgel 60F254, Merck, chloroform-methanol; 5:1).

FAB-MS(m/z): 768[M+H]$^+$.

(Step 3) Preparation of Compound (56)

26.7 mg of compound (55) was dissolved in 5 ml of ethyl acetate and stirred together with a catalytic amount of 10% palladium-carbon under a hydrogen atmosphere at room temperature. After 5 hours, 3 ml of acetic acid was added. Then, 4 hours later, 3 ml of methanol was further added, and the reaction was conducted for 1 hour. The reaction solution was filtered, mixed with 5 ml of sodium phosphate buffer (10 mM, pH 5.97) and washed with 10 ml of ethyl acetate. The ethyl acetate layer was washed with 5 ml of water twice. All the lower layers were combined and concentrated to 10 ml in vacuo for removal of ethyl acetate by evaporation. The concentrate was charged onto Diaion HP-20 (Mitsubishi Chemical, volume 3 ml), washed with 20 ml of water and eluted with 15 ml of methanol. The methanolic eluate was concentrated in vacuo to give 7.5 mg of compound (56) as a colorless solid.

Rf: 0.13 (Kieselgel 60F254, Merck, chloroform-methanol; 5:1).

FAB-MS(m/z): 602[M+H]$^+$.

$^1$H-NMR(δ ppm, 500 MHz, CDCl$_3$):9.81 (1H, s), 5.94 (1H, brd, J=3.7 Hz), 5.64(1H, brd, J=3.0 Hz), 4.88(1H, m), 4.21(1H, m), 4.16(1H, m), 4.00(1H, d, J=9.8 Hz), 3.92(1H, d, J=9.8 Hz), 3.78(2H, m), 3.63(1H, brs), 3.24(1H, m), 2.76(1H, m), 2.71(1H, t, J=3.7 Hz), 2.40 (1H, m), 2.23(1H, m), 1.50–2.10(13H, m), 1.20(2H, m), 1.00(1H, m), 0.98(3H, d, J=6.7 Hz), 0.95(3H, d, J=6.7 Hz), 0.76(3H, d, J=6.7 Hz).

EXAMPLE 32
Preparation of 8a-[[[6-(3-phenoxypropyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (59)

(Step 1) Preparation of 8a-[[[6-(3-phenoxypropyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (57)

49.5 mg of compound (6) was dissolved in 0.4 ml of dry dimethylformamide under a nitrogen atmosphere and mixed with about 7 mg of sodium hydride under cooling with ice. After 15 minutes, 40 μl of 3-phenoxypropyl bromide was added, and the reaction was conducted for 66 hours under stirring.

Then, the reaction solution was charged onto a silica gel column (Kieselgel 60, Merck, 1.5φ×25 cm) and eluted with n-hexane-ethyl acetate (4:1). The fraction containing the desired product was concentrated in vacuo to give 34.5 mg of compound (57) as a colorless oily substance.

Rf: 0.51 (Kieselgel 60F254, Merck, n-hexane-ethyl acetate; 2:1).

FAB-MS(m/z): 905[M+H]$^+$.

(Step 2) Preparation of 8a-[[[6-(3-phenoxypropyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (58)

34.5 mg of compound (57) was dissolved in 0.1 ml of dry tetrahydrofuran and stirred together with 60 μl of 1M tetrabutylammonium fluoride-tetrahydrofuran solution at room temperature for 115 minutes.

The reaction product was charged onto a silica gel column (Kieselgel 60, Merck, 1.5φ×13 cm) and eluted with n-hexane-ethyl acetate (2:1). The fraction containing the desired product was concentrated in vacuo to give 13.0 mg of compound (58) as a colorless oily substance.

Rf: 0.26 (Kieselgel 60F254, Merck, n-hexane-ethyl acetate; 2:1).

FAB-MS(m/z): 791[M+H]$^+$.

(Step 3) Preparation of Compound (59)

13.0 mg of compound (58) was dissolved in 2 ml of ethyl acetate and stirred together with a catalytic amount of 10% palladium-carbon under a hydrogen atmosphere at room temperature. After 30 minutes, the reaction solution was filtered and concentrated in vacuo. The reaction product was dissolved in 2 ml of methanol and washed with 2 ml of n-hexane twice, and the lower layer was concentrated in vacuo to give 6.6 mg of compound (59) as a colorless solid.

Rf: 0.49 (Kieselgel 60F254, Merck, chloroform-methanol; 10:1).

FAB-MS(m/z): 625[M+H]$^+$.

$^1$H-NMR(δ ppm, 500 MHz, CDCl$_3$):9.68(1H, s), 7.28 (2H, t, J=7.6 Hz), 6.95(1H, t, J=7.6 Hz), 6.90(2H, d, J=7.6 Hz), 6.06(1H, brd, 3.7 Hz), 5.69(1H, brd, J=3.0 Hz), 4.55 (1H, m), 4.31(1H, m), 4.09(2H, t, J=6.1 Hz), 4.03 (1H, d, J=9.8 Hz), 3.96(1H, d, J=9.8 Hz), 3.82(1H, m), 3.75(2H, m), 3.72(1H, brs), 2.75(1H, t, J=3.7 Hz), 2.33 (1H, m), 2.11(2H, m), 1.83–2.10(6H, m), 1.74(2H, m), 1.26(1H, d, J=12.5 Hz), 1.22(1H, m), 1.01(3H, d, J=6.7 Hz), 1.01(1H, m), 0.94(3H, d, J=6.7 Hz), 0.78(3H, d, J=6.7 Hz).

EXAMPLE 33
Preparation of 8a-[[[6-(3-(N-1H-pyrrolo)propyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (62)

(Step 1) Preparation of 8a-[[[6-(3-(N-1H-pyrrolo)propyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (60)

50.0 mg of compound (6) was dissolved in 0.4 ml of dry dimethylformamide under a nitrogen atmosphere and mixed with about 8 mg of sodium hydride under cooling with ice. After 20 minutes, 40 μl of 1-(3-bromopropyl)pyrrole was added, and the reaction was conducted at room temperature under stirring for 110 minutes.

Then, the reaction solution was charged onto a silica gel column (Kieselgel 60, Merck, 1.5φ×15 cm) and eluted with n-hexane-ethyl acetate (4:1). The fraction containing the desired product was concentrated in vacuo to give 47.2 mg of compound (60) as a colorless oily substance.

Rf: 0.40 (Kieselgel 60F254, Merck, n-hexane-ethyl acetate; 2:1).

FAB-MS(m/z): 878[M+H]$^+$.

(Step 2) Preparation of 8a-[[[6-(3-(N-1H-pyrrolo)propyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (61)

42.7 mg of compound (60) was dissolved in 0.2 ml of dry tetrahydrofuran and stirred together with 80 μl of 1M tetrabutylammonium fluoride-tetrahydrofuran solution at room temperature for 70 minutes.

The reaction product was charged onto a silica gel column (Kieselgel 60, Merck, 1.5φ×15 cm) and eluted with n-hexane-ethyl acetate (2:1). The fraction containing the desired product was concentrated in vacuo to give 36.0 mg of compound (61) as a colorless oily substance.

Rf: 0.29 (Kieselgel 60F254, Merck, n-hexane-ethyl acetate; 2:1).

FAB-MS(m/z): 764[M+H]$^+$.

(Step 3) Preparation of Compound (62)

36.0 mg of compound (61) was dissolved in a liquid mixture of 3 ml of ethyl acetate and 3 ml of methanol and stirred together with a catalytic amount of 10% palladium-carbon under a hydrogen atmosphere at room temperature. After 40 minutes, the reaction solution was filtered and concentrated in vacuo. The reaction product was dissolved in 5 ml of methanol and washed with 5 ml of n-hexane twice, and the lower layer was concentrated in vacuo to give 24.2 mg of compound (62) as a colorless solid.

Rf: 0.22 (Kieselgel 60F254, Merck, n-hexane-ethyl acetate; 1:1).

FAB-MS(m/z): 598[M+H]$^+$.

$^1$H-NMR(δ ppm, 500 MHz, CDCl$_3$):9.68(1H, s), 6.67 (2H, t, J=2.1 Hz), 6.14(2H, t, J=2.1 Hz), 6.11(1H, brd, J=3.7 Hz), 5.71(1H, brd, J=3.0 Hz), 4.54(1H, m), 4.28 (1H, m), 4.00–4.06(4H, m), 3.74(1H, brs), 3.69(1H, t, J=4.0 Hz), 3.55(1H, m), 3.44(1H, m), 2.83(1H, t, J=3.7 Hz), 2.34(1H, m), 1.90–2.10(7H, m), 1.87(1H, m), 1.76(2H, m), 1.20–1.30 (2H, m), 1.03(3H, d, J=6.7 Hz), 1.02(1H, m), 0.97(3H, d, J=6.7 Hz), 0.79(3H, d, J=6.7 Hz).

EXAMPLE 34
Preparation of 8a-[[[6-(cyanopropyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (65)

(Step 1) Preparation of 8a-[[[6-(cyanopropyloxy)tetrahydro-7-t-butyldimethylsilyloxy-2,5-methanofuro[2,3-d]-1,3- dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (63)

150.0 mg of compound (6) was dissolved in 0.4 ml of dry dimethylformamide under a nitrogen atmosphere and mixed with 14 mg of sodium hydride under cooling with ice. After 30 minutes, 100 μl of 4-bromobutyronitrile was added, and the reaction was conducted under cooling with ice under stirring for 2.5 hours.

Then, the reaction solution was charged onto a silica gel column (Kieselgel 60, Merck, 1.0ϕ×28 cm) and eluted with n-hexane-ethyl acetate (4:1). The fraction containing the desired product was concentrated in vacuo to give 27.3 mg of compound (63) as a colorless oily substance.

Rf: 0.71 (Kieselgel 60F254, Merck, n-hexane-ethyl acetate; 1:1).

FAB-MS(m/z): 860[M+Na]$^+$.

(Step 2) Preparation of 8a-[[[6-(cyanopropyloxy)tetrahydro-7-hydroxy-2,5-methanofuro[2,3-d]-1,3-dioxol-2-yl]oxy]methyl]-4-formyl- 4,4a,5,6,7,7a,8,8a-octahydro-7-methyl-3-(1-methylethyl)-1,4-methano-s-indacene-3a(1H)-carboxylic acid diphenylmethyl ester (64)

24 mg of compound (63) was dissolved in 1.0 ml of dry tetrahydrofuran and stirred together with 44 μl of 1M tetrabutylammonium fluoride-tetrahydrofuran solution at room temperature for 1.5 hours.

The reaction product was charged onto a silica gel column (Kieselgel 60, Merck, 1.0ϕ×21 cm) and eluted with n-hexane-ethyl acetate (2:1). The fraction containing the desired product was concentrated in vacuo to give 22.4 mg of compound (64) as a colorless oily substance.

Rf: 0.36 (Kieselgel 60F254, Merck, n-hexane-ethyl acetate; 2:1).

FAB-MS(m/z): 724[M+H]$^+$.

(Step 3) Preparation of Compound (65)

20 mg of compound (64) was dissolved in 3 ml of ethyl acetate and stirred together with a catalytic amount of 10% palladium-carbon under a hydrogen atmosphere at room temperature for 1.5 hours. The reaction solution was filtered and concentrated in vacuo. The reaction product was dissolved in 10 ml of methanol and washed with 10 ml of n-hexane four times, and the lower layer was concentrated in vacuo to give 4.2 mg of compound (65) as a colorless solid.

Rf: 0.15 (Kieselgel 60F254, Merck, n-hexane-ethyl acetate; 2:1).

FAB-MS(m/z): 558[M+H]$^+$.

$^1$H-NMR(δ ppm, 500 MHz, CDCl$_3$):9.64(1H, s), 6.09 (1H, brd, J=3.7 Hz), 5.72(1H, brd, J=3.0 Hz), 4.58(1H, m), 4.32(1H, m), 4.05(1H, d, J=9.8 Hz), 3.95(1H, d, J=9.8 Hz), 3.77(1H, t, J=4.0 Hz), 3.72(1H, m), 3.71(1H, brs), 3.68(1H, m), 2.74(1H, brs), 2.52(2H, t, J=7.3 Hz), 2.36(1H, m), 1.70–2.10(10H, m), 1.18–1.30(2H, m), 1.02(3H, d, J=6.7 Hz), 1.01(1H, m), 0.97(3H, d, J=6.7 Hz), 0.79(3H, d, J=6.7 Hz).

EXAMPLE 35

Preparation of 8a-[[[6-(ethoxycarbonylmethoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (68)

(Step 1) Preparation of 8a-[[[6-(ethoxycarbonylmethoxy) tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (66)

50.0 mg of compound (6) was dissolved in 0.65 ml of dry dimethylformamide under a nitrogen atmosphere and mixed with 4.6 mg of sodium hydride under cooling with ice. After 30 minutes, 36 μl of ethyl bromoacetate was added, and the reaction was conducted under cooling with ice under stirring for 3.0 hours.

Then, the reaction solution was charged onto a silica gel column (Kieselgel 60, Merck, 1.0ϕ×28 cm) and eluted with n-hexane-ethyl acetate (8:1). The fraction containing the desired product was concentrated in vacuo to give 27.3 mg of compound (66) as a colorless oily substance.

Rf: 0.50 (Kieselgel 60F254, Merck, n-hexane-ethyl acetate; 2:1).

FAB-MS(m/z): 879[M+Na]$^+$.

(Step 2) Preparation of 8a-[[[6-(ethoxycarbonylmethoxy) tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (67)

21 mg of compound (66) was dissolved in 0.8 ml of dry tetrahydrofuran and stirred together with 36 μl of 1M tetrabutylammonium fluoride-tetrahydrofuran solution at room temperature for 1.5 hours.

The reaction product was charged onto a silica gel column (Kieselgel 60, Merck, 1.0ϕ×20 cm) and eluted with n-hexane-ethyl acetate (2:1). The fraction containing the desired product was concentrated in vacuo to give 20.1 mg of compound (67) as a colorless oily substance.

Rf: 0.22 (Kieselgel 60F254, Merck, n-hexane-ethyl acetate; 2:1).

FAB-MS(m/z): 743[M+H]$^+$.

(Step 3) Preparation of Compound (68)

22.4 mg of compound (67) was dissolved in 3 ml of ethyl acetate and stirred together with a catalytic amount of 10% palladium-carbon under a hydrogen atmosphere at room temperature for 1.5 hours. The reaction solution was filtered and concentrated in vacuo. The reaction product was dissolved in 5 ml of methanol and washed with 5 ml of n-hexane twice, and the lower layer was concentrated in vacuo to give 6.8 mg of compound (68) as a colorless solid.

Rf: 0.15 (Kieselgel 60F254, Merck, n-hexane-ethyl acetate; 2:1).

FAB-MS(m/z): 577[M+H]$^+$.

$^1$H-NMR(δ ppm, 500 MHz, CDCl$_3$):9.67(1H, s), 6.10 (1H, brd, J=3.7 Hz), 5.70(1H, brd, J=3.0 Hz), 4.62(1H, m), 4.37(1H, m), 4.30(1H, d, J=16.8 Hz), 4.23(2H, t, J=7.0 Hz), 4.19(1H, d, J=16.8 Hz), 4.03(1H, d, J=9.8 Hz), 3.97(1H, d, J=9.8 Hz), 3.86(2H, m), 2.82(1H, t, J=3.7 Hz), 2.32(1H, m), 1.84–2.10(6H, m), 1.75(2H, m), 1.30(3H, t, J=7.0 Hz), 1.18–1.30(2H, m), 1.02(3H, d, J=6.7 Hz), 1.02(1H, m), 0.94(3H, d, J=6.7 Hz), 0.78(3H, d, J=6.7 Hz).

EXAMPLE 36

Preparation of 8a-[[[6-(aminocarbonylmethoxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (71)

(Step 1) Preparation of 8a-[[[6-(aminocarbonylmethoxy) tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (69)

50.0 mg of compound (6) was dissolved in 0.65 ml of dry dimethylformamide under a nitrogen atmosphere and mixed with 4.6 mg of sodium hydride under cooling with ice. After 30 minutes, 43 μl of bromoacetamide was added, and the reaction was conducted under cooling with ice under stirring for 3 hours.

Then, the reaction solution was charged onto a silica gel column (Kieselgel 60, Merck, 1.0ϕ×28 cm) and eluted with n-hexane-ethyl acetate (1:1) and then ethyl acetate. The fraction containing the desired product was concentrated in vacuo to give 32.5 mg of compound (69) as a colorless oily substance.

Rf: 0.13 (Kieselgel 60F254, Merck, n-hexane-ethyl acetate; 2:1).

FAB-MS(m/z): 828[M+H]$^+$.

(Step 2) Preparation of 8a-[[[6-(aminocarbonylmethoxy) tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (70)

21 mg of compound (69) was dissolved in 0.8 ml of dry tetrahydrofuran and stirred together with 60 μl of 1M tetrabutylammonium fluoride-tetrahydrofuran solution at room temperature for 3 hours.

The reaction product was charged onto a silica gel column (Kieselgel 60, Merck, 1.0φ×20 cm) and eluted with n-hexane-ethyl acetate (2:1). The fraction containing the desired product was concentrated in vacuo to give 17 mg of compound (70) as a colorless oily substance.

Rf: 0.30 (Kieselgel 60F254, Merck, ethyl acetate).

FAB-MS(m/z): 714[M+H]$^+$.

(Step 3) Preparation of Compound (71)

14 mg of compound (70) was dissolved in 3 ml of ethyl acetate and stirred together with a catalytic amount of 10% palladium-carbon under a hydrogen atmosphere at room temperature for 1.5 hours. The reaction solution was filtered and concentrated in vacuo. The reaction product was dissolved in 10 ml of methanol and washed with 10 ml of n-hexane four times, and the lower layer was concentrated in vacuo to give 8.6 mg of compound (71) as a colorless solid.

Rf: 0.15 (Kieselgel 60F254, Merck, ethyl acetate).

FAB-MS(m/z): 548[M+H]$^+$.

$^1$H-NMR(δ ppm, 500 MHz, CDCl$_3$):9.69(1H, s), 6.81 (1H, brs), 6.17(1H, brs), 6.10(1H, brd, J=3.7 Hz), 5.74 (1H, brd, J=3.0 Hz), 4.60(1H, m), 4.34(1H, m), 4.18(1H, d, J=15.6 Hz), 4.11(1H, d, J=15.6 Hz), 4.02(1H, d, J=9.8 Hz), 3.98(1H, d, J=9.8 Hz), 3.85(1H, t, J=4.0 Hz), 3.74(1H, brs), 2.81(1H, t, J=3.7 Hz), 2.34(1H, m), 1.93–2.12(5H, m), 1.86(1H, m), 1.75(2H, m), 1.31(1H, d, J=12.5 Hz), 1.23(1H, m), 1.03(3H, d, J=6.7 Hz), 1.03 (1H, m), 0.96(3H, d, J=6.7 Hz), 0.79(3H, d, J=6.7 Hz).

EXAMPLE 37

Preparation of 8a-[[[6-(hydroxypropyloxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (74)

(Step 1) Preparation of 8a-[[[6-(benzyloxypropyloxy) tetrahydro-7-t-butyldimethylsilyloxy-2,5-methanofuro[2,3-d]-1,3-dioxol-2-yl]oxy]methyl]-4-formyl-4,4a,5,6,7,7a,8, 8a-octahydro-7-methyl-3-(1-methylethyl)-1,4-methano-s-indacene-3a(1H)-carboxylic acid diphenylmethyl ester (72)

50.0 mg of compound (6) was dissolved in 0.65 ml of dry dimethylformamide under a nitrogen atmosphere and mixed with 4.6 mg of sodium hydride under cooling with ice. After 30 minutes, 57 μl of benzyl 3-bromopropyl ether was added, and the reaction was conducted under cooling with ice under stirring for 30 minutes.

Then, the reaction solution was charged onto a silica gel column (Kieselgel 60, Merck, 1.0φ×20 cm) and eluted with n-hexane-ethyl acetate (10:1) and then n-hexane-ethyl acetate (3:1). The fraction containing the desired product was concentrated in vacuo to give 50.7 mg of compound (72) as a colorless oily substance.

Rf: 0.62 (Kieselgel 60F254, Merck, n-hexane-ethyl acetate; 2:1).

FAB-MS(m/z): 941[M+Na]$^+$.

(Step 2) Preparation of 8a-[[[6-(benzyloxypropyloxy) tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (73)

50 mg of compound (72) was dissolved in 1.8 ml of dry tetrahydrofuran and stirred together with 81 μl of 1M tetrabutylammonium fluoride-tetrahydrofuran solution at room temperature for 2.5 hours.

The reaction product was charged onto a silica gel column (Kieselgel 60, Merck, 1.5φ×20 cm) and eluted with n-hexane-ethyl acetate (5:1). The fraction containing the desired product was concentrated in vacuo to give 42.3 mg of compound (73) as a colorless oily substance.

Rf: 0.26 (Kieselgel 60F254, Merck, n-hexane-ethyl acetate; 2:1).

FAB-MS(m/z): 805[M+H]$^+$.

(Step 3) Preparation of Compound (74)

38.3 mg of compound (73) was dissolved in 0.9 ml of ethyl acetate and stirred together with a catalytic amount of 10% palladium-carbon under a hydrogen atmosphere at room temperature for 2.5 hours. The reaction solution was filtered and concentrated in vacuo. The reaction product was dissolved in 10 ml of methanol and washed with 15 ml of n-hexane four times, and the lower layer was concentrated in vacuo to give 23.5 mg of compound (74) as a colorless solid.

Rf: 0.36 (Kieselgel 60F254, Merck, ethyl acetate).

FAB-MS(m/z): 549[M+H]$^+$.

$^1$H-NMR(δ ppm, 500 MHz, CDCl$_3$):9.66(1H, s), 6.15 (1H, brd, J=3.7 Hz), 5.72(1H, brd, J=3.0 Hz), 4.60(1H, m), 4.32(1H, m), 4.00(2H, s), 3.70–3.83(6H, m), 2.81 (1H, t, J=3.7 Hz), 2.33(1H, m), 1.93–2.12(5H, m), 1.74–1.90(5H, m), 1.30(1H, d, J=12.5 Hz), 1.23(1H, m), 1.05(1H, m), 1.03(3H, d, J=6.7 Hz), 0.97(3H, d, J=6.7 Hz), 0.79(3H, d, J=6.7 Hz).

EXAMPLE 38

Preparation of 8a-[[[6-(benzyloxy)tetrahydro-7-hydroxy-2, 5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (76)

(Step 1) Preparation of 8a-[[[6-(benzyloxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (75)

1.12 g of compound (3) was dissolved in 10 ml of dichloromethane and stirred together with 42.3 mg of sodium hydride at room temperature. 274.4 mg of benzyl chloride and 21.1 mg of sodium hydride were added after 0.5 hour and after 2 hours, respectively, and the reaction solution was stirred for another 2 hours.

Then, the reaction solution was mixed with 5 ml of methanol and 1.5 ml of 1N sodium hydroxide, then stirred for 3 hours and poured into 500 ml of 0.1M sodium phosphate buffer pH 5.5 and extracted with 500 ml of ethyl acetate. The ethyl acetate extract was concentrated in vacuo, charged onto a silica gel column (Kieselgel 60, Merck, 3.0φ×40 cm) and eluted with chloroform-methanol (200:1). The fraction containing the desired product was concentrated in vacuo to give 320 mg of a residue.

Then, the residue was charged onto a silica gel column (Kieselgel 60, Merck, 2.5φ×40 cm) and eluted with chloroform-n-hexane-ethyl acetate (1:2:1). The fraction containing the desired product was concentrated to dryness to give 91 mg of compound (75).

Rf: 0.41 (Kieselgel 60F254, Merck, n-hexane-ethyl acetate; 2:1).

FAB-MS(m/z): 747[M+H]+.

(Step 2) Preparation of Compound (76)

15 mg of compound (75) was dissolved in 1 ml of ethyl acetate and allowed to react in the presence of a catalytic amount of 10% palladium-carbon under stirring under a hydrogen atmosphere at room temperature for 1 hour. The reaction solution was filtered, and the filtrate was concentrated in vacuo. The reaction product was charged onto a silica gel column (Kieselgel 60, Merck, 1.0φ×30 cm) and eluted with chloroform-methanol (20:1). The fraction containing the desired product was concentrated to dryness to give 10.0 mg of compound (76).

Rf: 0.26 (Kieselgel 60F254, Merck, chloroform-methanol; 20:1).

FAB-MS(m/z): 581[M+H]+.

$^1$H-NMR($\delta$ ppm, 400 MHz, CDCl$_3$):9.68(1H, s), 7.31–7.38(5H, m), 6.12(1H, dd, J=3.4, 1.5 Hz), 5.66(1H, dd, J=3.4, 1.5 Hz), 4.74(1H, d, J=11.7 Hz), 4.62(1H, d, J=11.7 Hz), 4.53(1H, m), 4.17(1H, m), 4.04(1H, d, J=9.8 Hz), 3.98(1H, d, J=9.8 Hz), 3.76–3.78(2H, m), 2.83(1H, t, J=3.4 Hz), 2.33(1H, m), 1.94–2.10(5H, m), 1.87(1H, m), 1.72–1.80(2H, m), 1.18–1.32(2H, m), 1.03(3H, d, J=6.8 Hz), 1.01(1H, m), 0.96(3H, d, J=6.8 Hz), 0.78(3H, d, J=6.8 Hz).

EXAMPLE 39

Preparation of 8a-[[[6-(benzylaminocarboxy)tetrahydro-7-hydroxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid (79)

(Step 1) Preparation of 8a-[[[6-(benzylaminocarboxy)tetrahydro-7-t-butyldimethylsilyloxy-2,5-methanofuro[2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (77)

50 mg of compound (6) was dissolved in dry toluene under a nitrogen atmosphere and stirred together with 9.6 μl of benzyl isocyanate and a catalytic amount of dibutyltin diacetate at room temperature for 20 hours. After the reaction, the insolubles were filtered off, and the filtrate was concentrated in vacuo to give a residue.

Then, the residue was charged onto a silica gel column (Kieselgel 60, Merck, 1.0φ×30 cm) and eluted with n-hexane-ethyl acetate (4:1). The fraction containing the desired product was concentrated to dryness to give 40 mg of compound (77).

Rf: 0.53 (Kieselgel 60F254, Merck, n-hexane-ethyl acetate; 2:1).

FAB-MS(m/z): 904[M+H]+.

(Step 2) Preparation of 8a-[[[6-(benzylaminocarboxy) tetrahydro-7-hydroxy-2, 5-methanofuro [2,3-d]-1,3-dioxol-2-yl]oxy]methyl]-4-formyl-4,4a,5,6,7,7a,8,8a-octahydro-7-methyl-3-(1-methylethyl)-1,4-methano-s-indacene-3a(1H)-carboxylic acid diphenylmethyl ester (78)

40 mg of compound (77) was mixed with 1.0 ml of tetrahydrofuran and 66.4 μl of 1M tetrabutylammonium fluoride-tetrahydrofuran solution, and the reaction was conducted at room temperature under stirring for 1 hour.

The reaction solution was charged onto a silica gel column (Kieselgel 60, Merck, 1.0φ×30 cm) and eluted with n-hexane-ethyl acetate (2:1). The fraction containing the desired product was concentrated to dryness to give 32 mg of compound (78).

Rf: 0.55 (Kieselgel 60F254, Merck, n-hexane-ethyl acetate; 1:1).

FAB-MS(m/z): 790[M+H]+.

(Step 3) Preparation of Compound (79)

27 mg of compound (78) was dissolved in 2 ml of ethyl acetate and allowed to react in the presence of a catalytic amount of 10% palladium-carbon under stirring under a hydrogen atmosphere at room temperature for 3 hours. The reaction solution was filtered, and the filtrate was concentrated in vacuo. The reaction product was charged onto a silica gel column (Kieselgel 60, Merck, 1.0φ×30 cm) and eluted with chloroform-methanol (20:1). The fraction containing the desired product was concentrated to dryness to give 18.4 mg of compound (79).

Rf: 0.36 (Kieselgel 60F254, Merck, chloroform-methanol; 20:1).

FAB-MS(m/z): 624[M+H]+.

$^1$H-NMR($\delta$ ppm, 500 MHz, CDCl$_3$):9.69(1H, s), 7.26–7.36(5H, m), 6.09(1H, brd, J=3.7 Hz), 5.74(1H, brd, J=2.2 Hz), 5.24(1H, brt, J=5.8 Hz), 4.77(1H, t, J=3.7 Hz), 4.72(1H, m), 4.35–4.43(3H, m), 4.02(1H, d, J=9.8 Hz), 3.95(1H, d, J=9.8 Hz), 3.66(1H, brs), 2.80(1H, t, J=3.7 Hz), 2.32(1H, m), 1.90–2.12(5H, m), 1.87(1H, m), 1.74(2H, m), 1.29(1H, d, J=12.8 Hz), 1.23(1H, m), 1.02(3H, d, J=6.7 Hz), 1.02(1H, m), 0.95(3H, d, J=6.7 Hz), 0.78(3H, d, J=6.7 Hz).

FORMULATION EXAMPLE 1

10 parts of compound 14, 15 parts of heavy magnesium oxide and 75 parts of lactose were uniformly mixed to obtain a powdery or fine granular powder having a particle size of at most 350 μm. This powder was put into capsule containers to obtain a capsule drug.

FORMULATION EXAMPLE 2

45 parts of compound 14, 15 parts of starch, 16 parts of lactose, 21 parts of crystalline cellulose, 3 parts of polyvinyl alcohol and 30 parts of distilled water were uniformly mixed, then pulverized, granulated and dried and then sieved to obtain granules having a size with a diameter of from 1410 to 177 μm.

FORMULATION EXAMPLE 3

Granules were prepared in the same manner as in Formulation Example 2, and then 96 parts of the granules were mixed with 3 parts of calcium stearate and press-molded into tablets having a diameter of 10 mm.

FORMULATION EXAMPLE 4

90 parts of granules obtained by the method of Formulation Example 2 were mixed with 10 parts of crystalline cellulose and 3 parts of calcium stearate, press-molded into tablets having a diameter of 8 mm. Then, a suspension mixture of syrup gelatin and precipitated calcium carbonate was added thereto to give sugar-coated tablets.

FORMULATION EXAMPLE 5

1 part of compound 14, 49.5 parts of Macrogol 4,000 and 49.5 parts of Macrogol 400 were mixed and well kneaded to homogeneity to give an ointment.

FORMULATION EXAMPLE 6

5 parts of compound 14, 5 parts of miconazole, 15 parts of heavy magnesium oxide and 75 parts of lactose were uniformly mixed to obtain a powdery or fine granular powder having a particle size of at most 350 μm. This is powder was put into capsule containers to obtain a capsule drug.

FORMULATION EXAMPLE 7

35 parts of compound 14, 10 parts of miconazole, 15 parts of starch, 16 parts of lactose, 21 parts of crystalline cellulose, 30 parts of poly distilled water were uniformly mixed, then pulverized, granulated and dried and then sieved to obtain granules having a size with a diameter of from 1410 to 177 μm.

FORMULATION EXAMPLE 8

Granules were prepared in the same manner as in Formulation Example 7, and then 96 parts of the granules were mixed with 3 parts of calcium stearate and press-molded into tablets having a diameter of 10 mm.

FORMULATION EXAMPLE 9

90 parts of granules obtained by the method of Formulation Example 7 were mixed with 10 parts of crystalline cellulose and 3 parts of calcium stearate, press-molded into tablets having a diameter of 8 mm. Then, a suspension mixture of syrup gelatin and precipitated calcium carbonate was added thereto to give sugar-coated tablets.

FORMULATION EXAMPLE 10

0.3 part of compound 14, 0.3 part of miconazole, 2.4 parts of a nonionic surfactant and 97 parts of physiological saline were mixed under heating, put into ampoules and sterilized to give an injection.

FORMULATION EXAMPLE 11

0.5 part of compound 14, 0.5 part of miconazole, 49.5 parts of Macrogol 4,000 and 49.5 parts of Macrogol 400 were mixed and well kneaded to homogeneity to give an ointment.

REFERENCE EXAMPLE 1
Production of BE-31405

Fungus BE-31405 strain incubated on a slant agar plate was inoculated into four 500 ml Erlenmeyer flasks containing 110 ml of a culture medium (pH 6.0 before sterilization) comprising 0.3% polypeptone, 0.3% glucose, 1.0% wheat embryo, 0.5% gluten meal, 0.3% malt extract, 3.0% maltose, 0.2% sodium chloride, 0.1% sodium nitrate, 0.1% potassium dihydrogenphosphate, 0.05% magnesium sulfate, 0.0002% ferrous sulfate, 0.00004% cupric chloride, 0.00004% manganese chloride, 0.00004% cobalt chloride, 0.00008% zinc sulfate, 0.00008% sodium borate and 0.00024% ammonium molybdate and incubated on a rotary shaker (180 rpm) at 28° C. for 72 hours. 2 ml of these cultures were inoculated into each of fifty 500 ml Erlenmeyer flasks containing 110 ml of the above culture medium and incubated on a rotary shaker (180 rpm) at 28° C. for 72 hours.

The culture solution (about 5L) thus obtained was thermally sterilized at 90° C. for 10 minutes and filtered, and the filtrate was applied to a 1.2L Diaion HP-20 adsorption column. The column was washed with 30% methanol (4L), and 3L of methanol was applied to elute the active component. The methanolic eluate was concentrated in vacuo, and water was added to a total volume of 500 ml. It was extracted with 500 ml of ethyl acetate twice, and the resulting ethyl acetate extract was concentrated in vacuo to dryness. The resulting crude product was subjected to silica gel column chromatography (inner diameter 2 cm, length 30 cm, Kieselgel 60, Merck) and eluted with 400 ml (100:1) and 800 ml (50:1) of chloroform/methanol solvent mixtures successively. The fraction containing BE-31405 was concentrated in vacuo to dryness to give 320 mg of a crude product. Then, the crude product was subjected to reversed phase HPLC (Chromatolex-OSD (100 Å–5 μm), 20Φ×250 mm, Fuji Devison Chemical) using 70% aqueous methanol as the mobile phase, and the fraction corresponding to a peak identified at about 22 minutes by UV detection at 220 nm when the flow rate was 9 ml/min was collected and concentrated in vacuo to dryness. The resulting crude BE-31405 was subjected to Sephadex LH20 column chromatography (inner diameter 1.5 cm, length 90 cm) using methanol as the eluent, and the fraction containing pure BE-31405 was concentrated in vacuo to dryness to give BE-31405 as a white solid.

Production of BE-31405 using Penicillium sp. F31405-17M is shown in the following Reference Examples.

In the following Reference Examples, the separation and quantification of BE-31405 by high performance liquid chromatography (HPLC) were conducted under the following conditions.
HPLC conditions
   Column: YMC Pack ODS-A 250×4.6 mm I.D.
   Column temp.: 40° C.
   Mobile phase: 10% acetonitrile (containing 0.0375% trifluoroacetic acid)/80% acetonitrile (containing 0.025% trifluoroacetic acid)=55/45
   Retention time: 17 minutes
   Flow rate: 1.2 ml/min
   Detection: 220 nm

REFERENCE EXAMPLE 2

Spores from Penicillium sp. F-31405 strain incubated on a slant agar plate containing 0.2% potato exudate powder, 1% glucose and 1.5% agar (pH 5.6 before sterilization) were suspended in 10 ml of sterilized water and diluted with sterilized water by factors of 10, 100, 1000, 10000 and 100000. 0.2 ml of each dilute solution was spread on an agar plate and incubated at 25° C. for 4 days, and the viable colonies were transplanted onto slant agar plates and incubated at 25° C. for 14 days. Thus, a monosporous isolate from Penicillium sp. F-31405, the F31405-17M strain, was obtained. The monosporous isolate F31405-17M strain incubated on slant agar plates was inoculated into a 500 ml Erlenmeyer flasks containing 110 ml of a Czapek-Dox medium (pH 6.0 before sterilization) containing 3.6% glucose, 0.2% sodium nitrate, 0.1% dipotassium phosphate, 0.05% magnesium sulfate, 0.05% potassium chloride and 0.001% ferrous sulfate and incubated on a rotary shaker (180 rpm) at 28° C. for 72 hours. 2 ml of this culture was inoculated into a 500 ml Erlenmeyer flasks containing 110 ml of a modified medium A (pH 6.0 before sterilization) comprising 7.2% glucose, 0.2% sodium nitrate, 0.1% dipotassium phosphate, 0.1% magnesium sulfate, 0.05% potassium chloride, 2% yeast extract and 0.5% nicotinic acid and incubated on a rotary shaker (180 rpm) at 28° C. for 168 hours. 15 ml of the culture was extracted with 15 ml of ethyl acetate over 30 minutes under stirring. 10 ml of the ethyl acetate layer was evaporated in vacuo for removal of ethyl acetate, and the residue was dissolved in 1 ml of methanol. The BE-31405 concentration of the methanol solution was determined by high performance liquid chromatography.

REFERENCE EXAMPLE 3

The monosporous isolate from Penicillium sp. F-31405, the F31405-17M strain, incubated on a slant agar plate was inoculated into two 500 ml Erlenmeyer flasks containing 110 ml of a modified medium B (pH 6.0 before sterilization) comprising 7.2% glucose, 0.2% sodium nitrate, 0.1% dipotassium phosphate, 0.1% magnesium sulfate and 0.05% potassium chloride and incubated on a rotary shaker (180 rpm) at 28° C. for 72 hours. 200 ml of this culture was inoculated into a 20L fermenter containing 10L of a modified medium C (pH 6.0 before sterilization) comprising 7.2% glucose, 0.1% magnesium sulfate, 2% yeast extract and 0.2% nicotinic acid and incubated at 28° C. for 9 days with aeration (20 L/min) and stirring (300 rpm). 15 ml of this culture was extracted with 15 ml of ethyl acetate over 30 minutes under stirring. 10 ml of the ethyl acetate layer was evaporated for removal of ethyl acetate in vacuo, and the residue was dissolved in 1 ml of methanol. The BE-31405 concentration of the methanol solution was determined by high performance liquid chromatography.

INDUSTRIAL APPLICABILITY

The compounds or antifungal composition of the present invention have excellent antifungal activities and thus are useful as antifungal agents.

What is claimed is:

1. A compound represented by general formula (I) or a pharmaceutically acceptable salt or ester thereof:

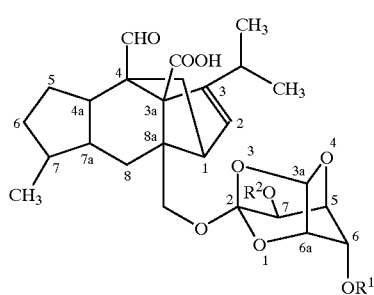

[I]

wherein each of $R^1$ and $R^2$ is independently a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —Y—$R^3$; Y is a carbonyl group, a thiocarbonyl group or a sulfonyl group; and $R^3$ is a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which is not substituted, or a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1$–$C_{16}$ alkyl group, a halo-$C_1$–$C_{16}$ alkyl group, a hydroxy-$C_1$–$C_{16}$ alkyl group, an amino-$C_1$–$C_{16}$ alkyl group, a carboxy-$C_1$–$C_{16}$ alkyl group or a protecting group provided that when $R^2$ is a hydrogen atom, $R^1$ is not a methyl group or an acetyl group; when $R^2$ is an acetyl group, $R^1$ is not a methyl group.

2. The compound according to claim 1, which is a compound represented by general formula (I-a):

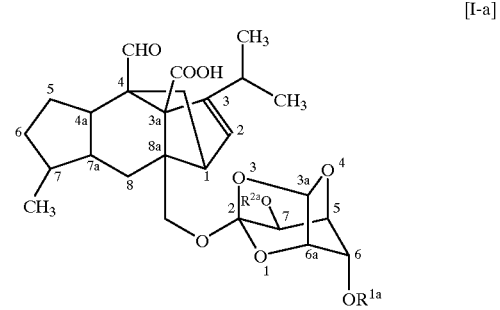

[I-a]

wherein $R^{1a}$ is a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —$Y^a$—$R^{3a}$; $Y^a$ is a carbonyl group, a thiocarbonyl group or a sulfonyl group; $R^{3a}$ is a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which is not substituted, or a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1$–$C_{16}$ alkyl group, a halo-$C_1$–$C_{16}$ alkyl group, a hydroxy-$C_1$–$C_{16}$ alkyl group, an amino-$C_1$–$C_{16}$ alkyl group, a carboxy-$C_1$–$C_{16}$ alkyl group or a protecting group; $R^{2a}$ is a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —$Y^b$—$R^{3b}$; $Y^b$ is a carbonyl group, a thiocarbonyl group or a sulfonyl group; and $R^{3b}$ is a $C_1$–$C_{16}$ alkyl group, a $C_2$–$C_{10}$ alkenyl group, a $C_3-C_6$ cycloalkyl group, a $C_3-C_6$ cycloalkyl-$C_1-C_{16}$ alkyl group, a $C_6-C_{12}$ aryl group, a $C_7-C_{15}$ aralkyl group, a $C_7-C_{15}$ aralkylamino group or a heterocyclic group which is not substituted, or a $C_1-C_{16}$ alkyl group, a $C_2-C_{10}$ alkenyl group, a $C_3-C_6$ cycloalkyl group, a $C_3-C_6$ cycloalkyl-$C_1-C_{16}$ alkyl group, a $C_6-C_{12}$ aryl group, a $C_7-C_{15}$ aralkyl group, a $C_7-C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1-C_{16}$ alkyl group, a halo-$C_1-C_{16}$ alkyl group, a hydroxy-$C_1-C_{16}$ alkyl group, an amino-$C_1-C_{16}$ alkyl group, a carboxy-$C_1-C_{16}$ alkyl group or a protecting group provided that when $Y^b$ is a carbonyl group, and $R^{3b}$ is a $C_1-C_{16}$ alkyl group which is not substituted, $R^{1a}$ is not a $C_1-C_{16}$ alkyl group which is not substituted.

3. The compound according to claim 1, which is a compound represented by general formula (I-b):

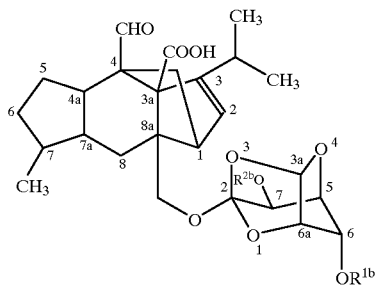

[I-b]

wherein $R^{1b}$ is a $C_1-C_{16}$ alkyl group which is not substituted; $R^{2b}$ is a group represented by —$Y^c$—$R^{3c}$; $Y^c$ is a carbonyl group; and $R^{3c}$ is a $C_1-C_{16}$ alkyl group which is not substituted provided that both $R^{1b}$ and $R^{3c}$ are not methyl groups at the same time.

4. The compound according to claim 1, which is a compound represented by general formula (I-c):

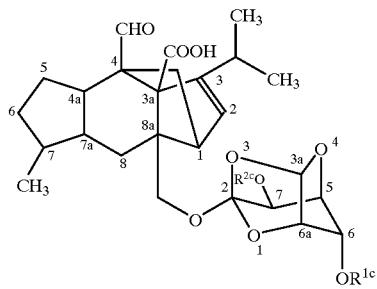

[I-c]

wherein $R^{1c}$ is a hydrogen atom, a $C_2-C_{10}$ alkenyl group, a $C_3-C_6$ alkynyl group, a $C_6-C_{12}$ aryl group, a $C_7-C_{15}$ aralkyl group or a heterocyclic group, or a $C_1-C_{16}$ alkyl group, a $C_2-C_{10}$ alkenyl group, a $C_3-C_6$ alkynyl group, a $C_6-C_{12}$ aryl group, a $C_7-C_{15}$ aralkyl group or a heterocyclic group which has one to five substituents selected from the group consisting of halogen atoms, cyano groups, hydroxyl groups, $C_1-C_{16}$ alkyloxy groups, $C_1-C_{16}$ alkylcarbonyloxy groups, amino groups, mono-$C_1-C_{16}$ alkylamino groups, di-$C_1-C_{16}$ alkylamino groups, carboxyl groups, $C_1-C_{16}$ alkyloxycarbonyl groups, aminocarbonyl groups, sulfo groups, $C_6-C_{12}$ aryl groups, $C_6-C_{12}$ aryloxy groups, $C_7-C_{15}$ aralkyloxy groups and heterocyclic groups, or a group represented by —Y—$R^3$; Y is a carbonyl group, a thiocarbonyl group or a sulfonyl group; $R^3$ is a $C_1-C_{16}$ alkyl group, a $C_2-C_{10}$ alkenyl group, a $C_3-C_6$ cycloalkyl group, a $C_3-C_6$ cycloalkyl-$C_1-C_{16}$ alkyl group, a $C_6-C_{12}$ aryl group, a $C_7-C_{15}$ aralkylamino group, a $C_7-C_{15}$ aralkylamino group or a heterocyclic group which is not substituted, or a $C_1-C_{16}$ alkyl group, a $C_2-C_{10}$ alkenyl group, a $C_3-C_6$ cycloalkyl group, a $C_3-C_6$ cycloalkyl-$C_1-C_{16}$ alkyl group, a $C_6-C_{12}$ aryl group, a $C_7-C_{15}$ aralkyl group, a $C_7-C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1-C_{16}$ alkyl group, a halo-$C_1-C_{16}$ alkyl group, a hydroxy-$C_1-C_{16}$ alkyl group, an amino-$C_1-C_{16}$ alkyl group, a carboxy-$C_1-C_{16}$ alkyl group or a protecting group; and $R^{2c}$ is a hydrogen atom provided that when Y is a carbonyl group, $R^3$ is not a $C_1-C_{16}$ alkyl group which is not substituted.

5. The compound according to claim 1, which is a compound represented by general formula (I-d):

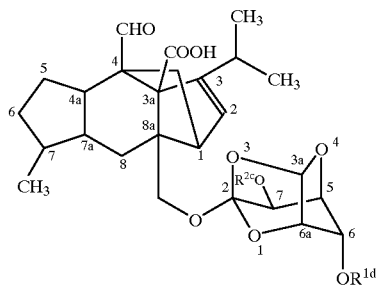

[I-d]

wherein $R^{1d}$ is a $C_1-C_{16}$ alkyl group which is not substituted; and $R^{2c}$ is a hydrogen atom provided that $R^{1d}$ is not a methyl group.

6. The compound according to claim 5, wherein $R^{1d}$ is a $C_4-C_{10}$ alkyl group which is not substituted.

7. The compound according to claim 5, wherein $R^{1d}$ is a butyl group, a pentyl group, an isopentyl group, a hexyl group or a decyl group.

8. The compound according to claim 1, which is a compound represented by general formula (I-e):

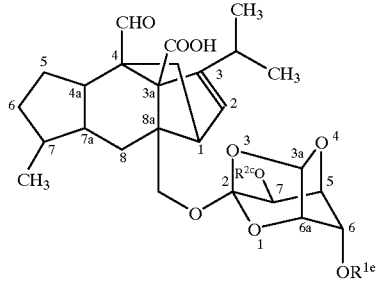

[I-e]

wherein $R^{1e}$ is a group represented by —$Y^c$—$R^{3d}$; $Y^c$ is a carbonyl group; $R^{3d}$ is a $C_1-C_{16}$ alkyl group which is not substituted; and $R^{2c}$ is a hydrogen atom provided that $R^{3d}$ is not a methyl group.

9. The compound according to claim 8, wherein $R^{3d}$ is a $C_3-C_9$ alkyl group which is not substituted.

10. The compound according to claim 8, wherein $R^{3d}$ is a propyl group, a butyl group, a pentyl group, a hexyl group or a nonyl group.

11. An antifungal agent containing a compound represented by general formula (I) or a pharmaceutically acceptable salt or ester thereof:

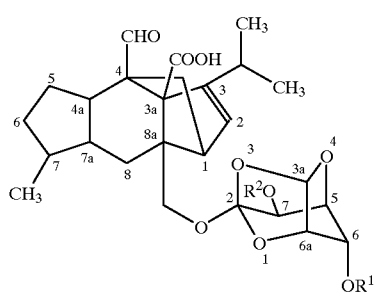

[I]

wherein each of $R^1$ and $R^2$ is independently a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —Y—$R^3$; Y is a carbonyl group, a thiocarbonyl group or a sulfonyl group; and $R^3$ is a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which is not substituted, or a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1$–$C_{16}$ alkyl group, a halo-$C_1$–$C_{16}$ alkyl group, a hydroxy-$C_1$–$C_{16}$ alkyl group, an amino-$C_1$–$C_{16}$ alkyl group, a carboxy-$C_1$–$C_{16}$ alkyl group or a protecting group, provided that when $R^2$ is a hydrogen atom, $R^1$ is not a methyl group or an acetyl group; when $R^2$ is an acetyl group, $R^1$ is not a methyl group, as an active ingredient.

12. An antifungal composition containing a compound represented by general formula (I) or a pharmaceutically acceptable salt or ester thereof:

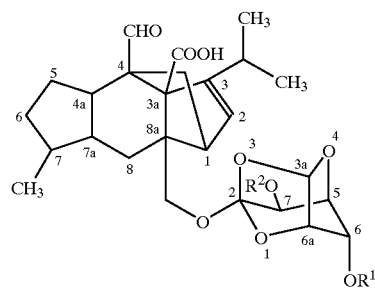

[I]

wherein each of $R^1$ and $R^2$ is independently a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —Y—$R^3$; Y is a carbonyl group, a thiocarbonyl group or a sulfonyl group; and $R^3$ is a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which is not substituted, or a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1$–$C_{16}$ alkyl group, a halo-$C_1$–$C_{16}$ alkyl group, a hydroxy-$C_1$–$C_{16}$ alkyl group, an amino-$C_1$–$C_{16}$ alkyl group, a carboxy-$C_1$–$C_{16}$ alkyl group or a protecting group, provided that when $R^2$ is a hydrogen atom, $R^1$ is not a methyl group or an acetyl group; when $R^2$ is an acetyl group, $R^1$ is not a methyl group, and an azole type antifungal agent, as active ingredients.

13. The antifungal composition according to claim 12, wherein the azole type antifungal agent is butoconazole, oxiconazole, clotrimazole, terconazole, econazole, tioconazole, miconazole, fluconazole, ketoconazole or itraconazole.

14. The antifungal composition according to claim 12, wherein the weight ratio of the compound represented by general formula (I) or a pharmaceutically acceptable salt or ester thereof:

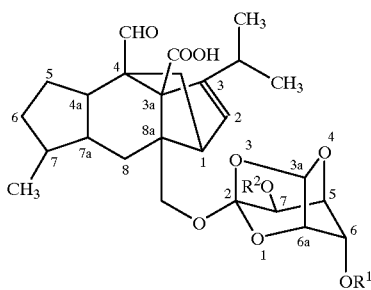

[I]

wherein each of $R^1$ and $R^2$ is independently a hydrogen atom, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which is not substituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group or a heterocyclic group which has one to five substituents selected from the group consisting of halogen atoms, cyano groups, hydroxyl groups, $C_1$–$C_{16}$ alkyloxy groups, $C_1$–$C_{16}$ alkylcarbonyloxy groups, amino groups, mono-$C_1$–$C_{16}$ alkylamino groups, di-$C_1$–$C_{16}$ alkylamino groups, carboxyl groups, $C_1$–$C_{16}$ alkyloxycarbonyl groups, aminocarbonyl groups, sulfo groups, $C_6$–$C_{12}$ aryl groups, $C_6$–$C_{12}$ aryloxy groups, $C_7$–$C_{15}$ aralkyloxy groups and heterocyclic groups, or a group represented by —Y—$R^3$; Y is a carbonyl group, a thiocarbonyl group or a sulfonyl group; and $R^3$ is a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which is not substituted, or a $C_1$–$C_{16}$ alkyl group, a $C_2$–$C_{10}$ alkenyl group, a $C_3$–$C_6$ cycloalkyl group, a $C_3$–$C_6$ cycloalkyl-$C_1$–$C_{16}$ alkyl group, a $C_6$–$C_{12}$ aryl group, a $C_7$–$C_{15}$ aralkyl group, a $C_7$–$C_{15}$ aralkylamino group or a heterocyclic group which has one to four substituents selected from the group consisting of halogen atoms, cyano groups, hydroxyl groups, amino groups and carboxyl groups, and hydroxyl groups, amino groups and carboxyl groups having a $C_1$–$C_{16}$ alkyl group, a halo-$C_1$–$C_{16}$ alkyl group, a hydroxy-$C_1$–$C_{16}$ alkyl group, an amino-$C_1$–$C_{16}$ alkyl group, a carboxy-$C_1$–$C_{16}$ alkyl group or a protecting group, provided that when $R^2$ is a hydrogen atom, $R^1$ is not a methyl group or an acetyl group; when $R^2$ is an acetyl group, $R^1$ is not a methyl group, to the azole type antifungal agent is from 0.001:1 to 1000:1.

* * * * *